(12) United States Patent
La Rota et al.

(10) Patent No.: US 12,077,766 B2
(45) Date of Patent: Sep. 3, 2024

(54) MADS BOX PROTEINS AND IMPROVING AGRONOMIC CHARACTERISTICS IN PLANTS

(71) Applicant: PIONEER HI-BRED INTERNATIONAL, INC., Johnston, IA (US)

(72) Inventors: Carlos M La Rota, Johnston, IA (US); Rosana Melo, St. Charles, MO (US); Bo Shen, Johnston, IA (US); Carl Simmons, Des Moines, IA (US); Jingrui Wu, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 17/047,518

(22) PCT Filed: Apr. 17, 2019

(86) PCT No.: PCT/US2019/027782
§ 371 (c)(1),
(2) Date: Oct. 14, 2020

(87) PCT Pub. No.: WO2019/204373
PCT Pub. Date: Oct. 24, 2019

(65) Prior Publication Data
US 2021/0155951 A1    May 27, 2021

Related U.S. Application Data

(60) Provisional application No. 62/783,309, filed on Dec. 21, 2018, provisional application No. 62/741,529, filed on Oct. 4, 2018, provisional application No. 62/659,579, filed on Apr. 18, 2018.

(51) Int. Cl.
*C12N 15/82* (2006.01)

(52) U.S. Cl.
CPC ................. *C12N 15/8269* (2013.01)

(58) Field of Classification Search
None
See application file for complete search history.

(56) References Cited

U.S. PATENT DOCUMENTS

| | | | |
|---|---|---|---|
| 6,504,083 B1 | 1/2003 | Barbour et al. | |
| 11,124,801 B2 | 9/2021 | Coles et al. | |
| 11,421,242 B2 | 8/2022 | Christensen et al. | |
| 2007/0270578 A1* | 11/2007 | Frankard | C12N 15/8261 800/290 |
| 2010/0175146 A1 | 7/2010 | Bruce et al. | |
| 2017/0240915 A1 | 8/2017 | Zhou et al. | |
| 2021/0155949 A1 | 5/2021 | Abbitt et al. | |
| 2021/0171971 A1 | 6/2021 | Haug Collet et al. | |
| 2021/0388370 A1 | 12/2021 | Coles et al. | |
| 2022/0380794 A1 | 12/2022 | Christensen et al. | |

FOREIGN PATENT DOCUMENTS

| | | |
|---|---|---|
| WO | 2000/037488 A2 | 6/2000 |
| WO | WO-2014208508 A1 | 12/2014 |

OTHER PUBLICATIONS

Genbank locus: ONM59473 (Year: 2017).*
Guo et al. "Protein tolerance to random amino acid change". PNAS 101: p. 9205-9210 (Year: 2004).*
International Search Report and Written Opinion for International Application PCT/US2019/027782, mailed Sep. 3, 2019.
Kyte. 1982. A simple method for displaying the hydropathic character of a protein. Journal of Molecular Biology, 157 (1), pp. 105-132.

\* cited by examiner

*Primary Examiner* — Matthew R Keogh
*Assistant Examiner* — David R Byrnes

(57) ABSTRACT

Provided are compositions comprising polynucleotides encoding polypeptides. Also provided are recombinant DNA constructs, plants, plant cells, seed, grain comprising the polynucleotides, and plants, plant cells, seed, grain comprising a genetic modification at a genomic locus encoding a polypeptide. Additionally, various methods of employing the polynucleotides and genetic modifications in plants, such as methods for modulating expression level in a plant and methods for increasing yield of a plant are also provided herein.

14 Claims, 3 Drawing Sheets

Figure 1:
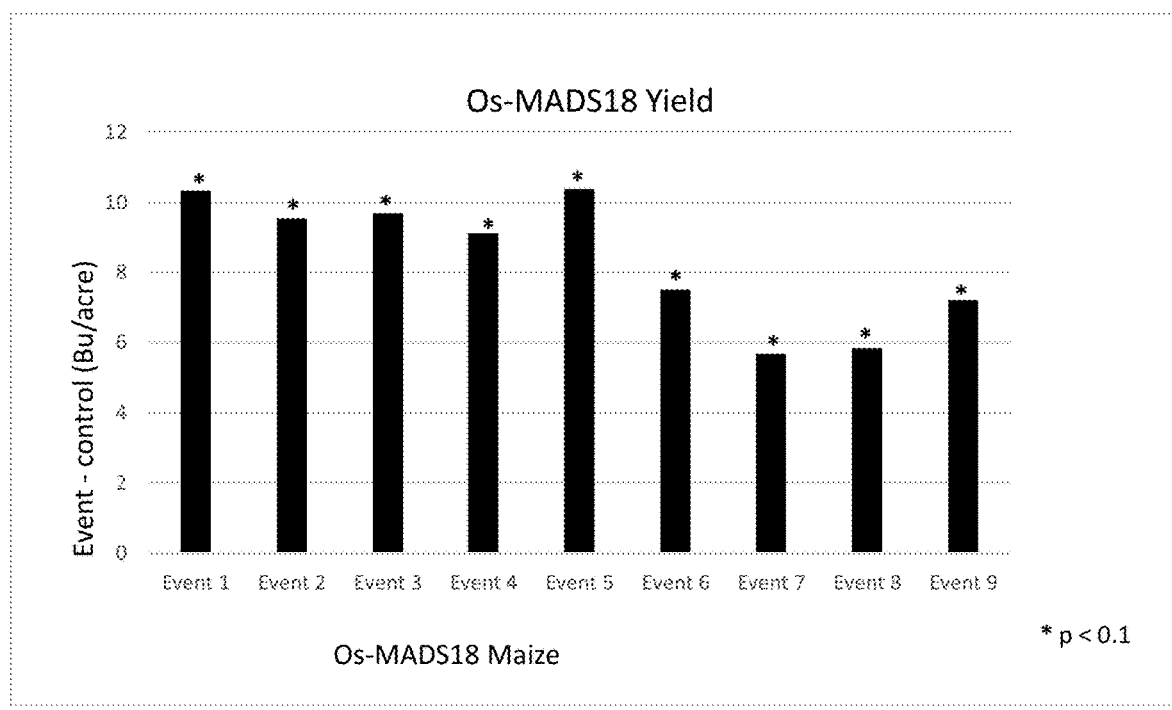

Specification includes a Sequence Listing.

MADS BOX PROTEINS AND IMPROVING AGRONOMIC CHARACTERISTICS IN PLANTS

The official copy of the sequence listing is submitted electronically via EFS-Web as an ASCII formatted sequence listing with a file named 7845WOPCT_ST25.txt created on Apr. 11, 2019 and having a size of 118 kilobytes and is filed concurrently with the specification. The sequence listing comprised in this ASCII formatted document is part of the specification and is herein incorporated by reference in its entirety.

FIELD

This disclosure relates to compositions and methods for improving yield in plants.

BACKGROUND

Global demand and consumption of agricultural crops is increasing at a rapid pace. Accordingly, there is a need to develop new compositions and methods to increase yield in plants. This invention provides such compositions and methods. Various plant MADS-box polypeptides are provided herein.

SUMMARY

Provided herein are polynucleotides encoding a polypeptide comprising an amino acid sequence that is at least 95% to 99% identical to an amino acid or the full length sequence selected from the group consisting of SEQ ID NOS: 1-10, 12-51.

Also provided are recombinant DNA constructs comprising a regulatory element operably linked to a polynucleotide encoding a polypeptide comprising an amino acid sequence that is at least 80% identical to an amino acid sequence or the full length sequence selected from the group consisting of SEQ ID NOS: 1-10, 12-51. In certain embodiments the regulatory element is a heterologous promoter, such as for example, GOS2 moderately constitutive promoter.

Provided are plant cells, plants, and seeds comprising the polynucleotide encoding a polypeptide or the recombinant DNA construct comprising a regulatory element operably linked to the polynucleotide encoding a polypeptide. In certain embodiments, the regulatory element is a heterologous promoter. In certain embodiments, the plant and/or seed is from a monocot plant. In certain embodiments, the plant is a monocot plant. In certain embodiments, the monocot plant is maize.

Further provided are plant cells, plants, and seeds comprising a targeted genetic modification at a genomic locus that encodes a polypeptide comprising an amino acid sequence that is at least 80% identical to an amino acid sequence selected from the group consisting of SEQ ID NOS: 1-10, 12-51, wherein the genetic modification increases the level and/or activity of the encoded polypeptide. In certain embodiments, the genetic modification is selected from the group consisting of an insertion, deletion, single nucleotide polymorphism (SNP), and a polynucleotide modification. In certain embodiments the targeted genetic modification is present in (a) the coding region; (b) a non-coding region; (c) a regulatory sequence; (d) an untranslated region; or (e) any combination of (a)-(d) of the genomic locus that encodes the polypeptide. In certain embodiments, the plant and/or seed is from a monocot plant. In certain embodiments, the plant is a monocot plant. In certain embodiments, the monocot plant is maize.

Provided are methods for increasing yield in a plant by expressing in a regenerable plant cell a recombinant DNA construct comprising a regulatory element operably linked to a polynucleotide encoding a polypeptide comprising an amino acid sequence that is at least 80% identical to an amino acid sequence selected from the group consisting of SEQ ID NOS: 1-10, 12-51; and generating the plant, wherein the plant comprises in its genome the recombinant DNA construct. In certain embodiments, the regulatory element is a heterologous promoter. In certain embodiments, the plant is a monocot plant. In certain embodiments, the monocot plant is maize. In certain embodiments, the yield is grain yield.

Further provided are methods for increasing yield in a plant by introducing in a regenerable plant cell a targeted genetic modification at a genomic locus that encodes a polypeptide comprising an amino acid sequence that is at least 80%, 85%, 90%, 91%, 92%, 93%, 94%, 95%, 96%, 97%, 98%, 99% identical to an amino acid sequence or the full length sequence selected from the group consisting of SEQ ID NOS: 1-10, 12-51; and generating the plant, wherein the level and/or activity of the encoded polypeptide is increased in the plant. In certain embodiments, the genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), an engineered site-specific meganucleases, or an Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes the polypeptide. In certain embodiments, the plant cell is from a monocot plant. In certain embodiments, the monocot plant is maize. In certain embodiments, the yield is grain yield.

Provided are methods for increasing photosynthetic activity in a plant by expressing in a regenerable plant cell a recombinant DNA construct comprising a regulatory element operably linked to a polynucleotide encoding a polypeptide comprising an amino acid sequence that is at least 80% to 98% identical to an amino acid sequence selected from the group consisting of SEQ ID NOS: 1-10, 12-51; and generating the plant, wherein the plant comprises in its genome the recombinant DNA construct. In certain embodiments, the regulatory element is a heterologous promoter. In certain embodiments, the plant is a monocot plant. In certain embodiments, the monocot plant is maize.

Also provided are methods for increasing photosynthetic activity in a plant by introducing in a regenerable plant cell a targeted genetic modification at a genomic locus that encodes a polypeptide comprising an amino acid sequence that is at least 80% to about 98% identical to an amino acid sequence selected from the group consisting of SEQ ID NOS: 1-10, 12-51; and generating the plant, wherein the level and/or activity of the encoded polypeptide is increased in the plant. In certain embodiments, the genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), an engineered site-specific meganucleases, or an Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes the polypeptide. In certain embodiments, the plant cell is from a monocot plant. In certain embodiments, the monocot plant is maize.

BRIEF DESCRIPTION OF THE DRAWINGS AND SEQUENCE LISTING

FIG. 1 demonstrates yield from nine maize lines that have increased expression of Os-MADS18 across multiple locations yield testing. Values plotted are bushels/acre yield increase of transgenic events over controls. *indicates P<0.1. Base yield (yield of controls) was 184 bushels/acre. Data are shown with BLUP analysis across 8 locations.

Figure 2:
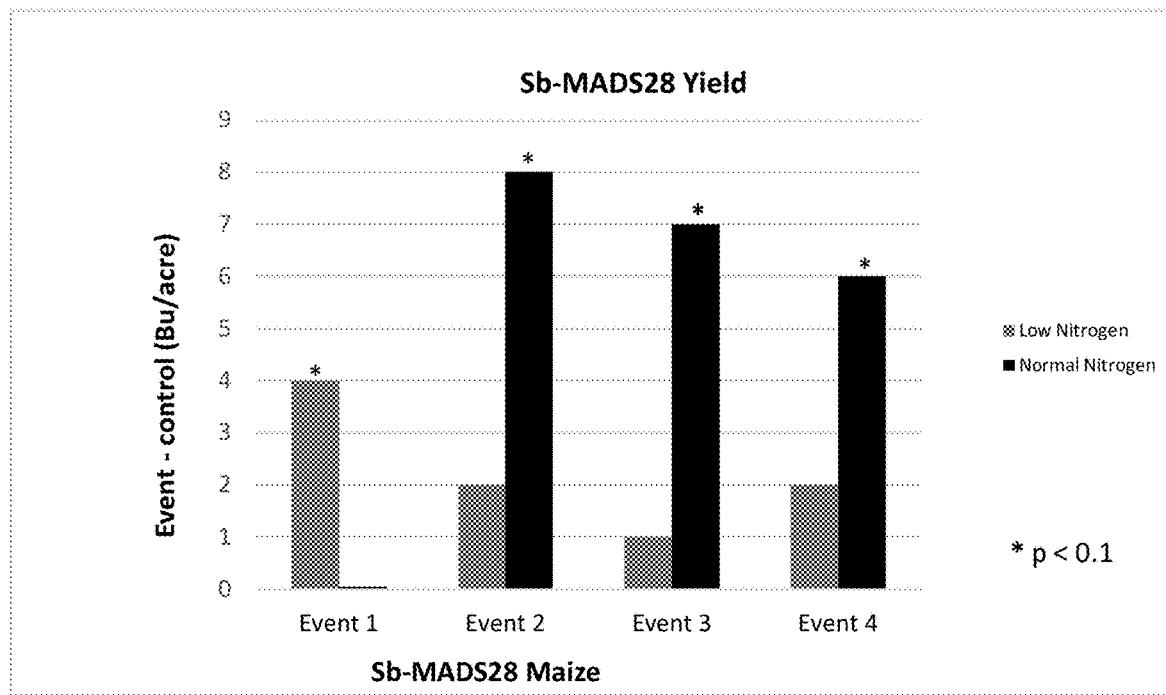

FIG. 2 demonstrates yield from four maize lines having increased expression of SB-MADS28 across multiple locations yield testing. Values plotted are bushels/acre yield increase of transgenic events over controls. *indicates P<0.1. Base yield (yield of controls) was 142 bushels/acre in low N condition and 172 bushels/acre under normal nitrogen condition. Data are shown with BLUP analysis.

Figure 3:
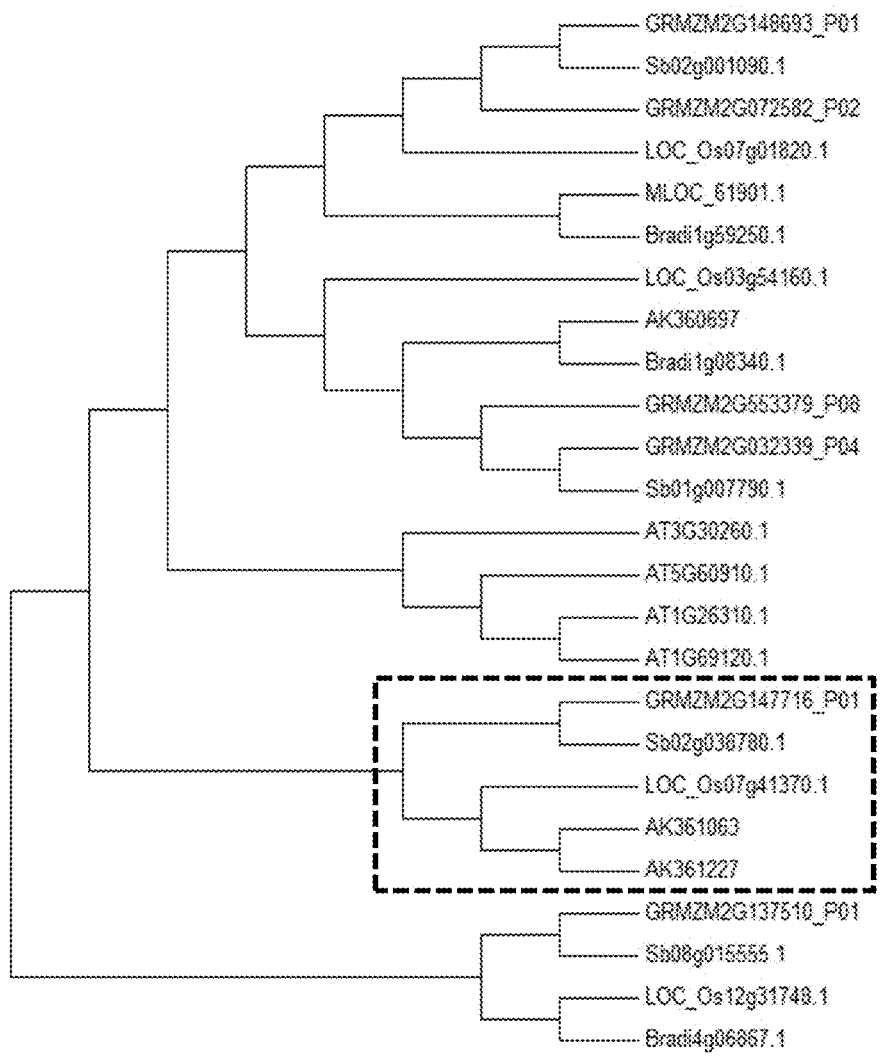

FIG. 3 shows phylogenetic tree of related MADS box proteins. Phylogenetic analysis of ZMM28 (Zm00001d022088) with AP1-FUL clade members from Arabidopsis and representative monocots. The clade containing ZMM28 is highlighted.

The disclosure can be more fully understood from the following detailed description and the accompanying drawings and Sequence Listing, which form a part of this application.

The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

TABLE 1

Sequence Listing

| SEQ ID NOS | DESCRIPTION | % Identity to SEQ ID NO: 11 |
|---|---|---|
| SEQ ID NO: 1 | OsMADS18 amino acid | 75 |
| SEQ ID NO: 2 | SB-MADS28 amino acid | 94 |
| SEQ ID NO: 3 | ZM-ZMM28 (ALT1) | 99 |
| SEQ ID NO: 4 | ZM-MADS27 (MOD) | 41 |
| SEQ ID NO: 5 | ZM-ANR1PT | 38 |
| SEQ ID NO: 6 | OS-MADS BOX GENOMIC (ALT1) AA Sequence | 75 |
| SEQ ID NO: 7 | OS-MADS BOX GENOMIC (ALT2) AA Sequence | 75 |
| SEQ ID NO: 8 | OS-MADS BOX GENOMIC (ALT3) AA Sequence | 75 |
| SEQ ID NO: 9 | OS-MADS BOX GENOMIC (ALT4) AA Sequence | 74 |
| SEQ ID NO: 10 | ZMM28 MO17 isoform | 99 |
| SEQ ID NO: 11 | Zmm28 Maize | 100 |
| SEQ ID NO: 12 | Zmm28-truncated Maize | 75 |
| SEQ ID NO: 13 | APL3 *Panicum virgatum* | 87 |
| SEQ ID NO: 14 | MADS-box transcription factor (*Setaria italica*) | 87 |
| SEQ ID NO: 15 | MADS-box transcription factor *Dichanthelium oligosanthes* | 85 |
| SEQ ID NO: 16 | MADS-box protein *Phyllostachys edulis* | 80 |
| SEQ ID NO: 17 | MADS-box transcription factor *Brachypodium distachyon* | 80 |
| SEQ ID NO: 18 | *Phyllostachys praecox* | 79 |
| SEQ ID NO: 19 | Agamous-like MADS-box protein *Zea mays* | 79 |
| SEQ ID NO: 20 | MADS-box protein *Hordeum vulgare* subsp. *Vulgare* | 78 |
| SEQ ID NO: 21 | MADS-box transcription factor *Aegilops tauschii* subsp. *Tauschii* | 77 |
| SEQ ID NO: 22 | *Triticum aestivum* MADS-box transcription factor | 77 |
| SEQ ID NO: 23 | *Brachypodium distachyon* | 77 |
| SEQ ID NO: 24 | MADS-box transcription factor *Triticum aestivum* | 76 |
| SEQ ID NO: 25 | MADS *Lolium perenne* | 76 |
| SEQ ID NO: 26 | MADS box transcription factor *Oryza sativa* EEC82413.1 | 74 |
| SEQ ID NO: 27 | MADS-box transcription factor *Brachypodium distachyon* AIG21814.1 | 73 |
| SEQ ID NO: 28 | MADS-box transcription factor *Oryza brachyantha* | 72 |
| SEQ ID NO: 29 | MADS *Hordeum vulgare* subsp. *Vulgare* | 72 |
| SEQ ID NO: 30 | MADS-box transcription factor *Aegilops tauschii* subsp. *Tauschii* | 71 |
| SEQ ID NO: 31 | MADS-box transcription factor *Phoenix dactylifera* | 62 |
| SEQ ID NO: 32 | MADS-box transcription factor *Elaeis guineensis* | 62 |
| SEQ ID NO: 33 | MADS-box transcription factor *Ananas comosus* | 62 |
| SEQ ID NO: 34 | *Alstroemeria ligtu* subsp. *Ligtu* | 61 |
| SEQ ID NO: 35 | Transcription factor *Musa acuminata* subsp. *Malaccensis* | 61 |
| SEQ ID NO: 36 | *Tricyrtis* sp. *Shinonome* | 61 |
| SEQ ID NO: 37 | Transcription factor *Musa acuminata* subsp. *Malaccensis* (truncated) | 61 |
| SEQ ID NO: 38 | APETALA1-like protein *Alpinia oblongifolia* | 60 |
| SEQ ID NO: 39 | MADS-box transcription factor *Crocus sativus* | 60 |
| SEQ ID NO: 40 | Truncated transcription factor *Ananas comosus* | 59 |
| SEQ ID NO: 41 | Truncated transcription factor *Dendrobium catenatum* | 59 |
| SEQ ID NO: 42 | Truncated transcription factor *Phalaenopsis equestris* | 59 |
| SEQ ID NO: 43 | *Lilium formosanum* x *Lilium longiflorum* | 58 |
| SEQ ID NO: 44 | MADS-box protein *Dendrobium nobile* | 58 |
| SEQ ID NO: 45 | Transcription factor *Musa acuminata* subsp. *Malaccensis* | 57 |

TABLE 1-continued

Sequence Listing

| SEQ ID NOS | DESCRIPTION | % Identity to SEQ ID NO: 11 |
|---|---|---|
| SEQ ID NO: 46 | Transcription factor *Ricinus communis* | 57 |
| SEQ ID NO: 47 | *Vitis vinifera* | 57 |
| SEQ ID NO: 48 | MADS-box transcription factor *Tulipa gesneriana* | 56 |
| SEQ ID NO: 49 | MADS box transcription factor *Daucus carota* subsp. *Sativus* | 56 |
| SEQ ID NO: 50 | *Papaver atlanticum* | 56 |
| SEQ ID NO: 51 | *Theobroma cacao* | 55 |
| SEQ ID NO: 52 | OsMADS18 genomic DNA | N/A |

I. Compositions

A. Polynucleotides and Polypeptides

The present disclosure provides polynucleotides encoding polypeptides. Accordingly, as used herein "polypeptide," "protein," or the like, refers to a protein represented by a SEQ ID NO.

One aspect of the disclosure provides a polynucleotide encoding a polypeptide comprising an amino acid sequence that is at least 80-99%% identical to the amino acid sequence of any one of SEQ ID NOS: 1-10, 12-51).

Phylogenetic analysis of ZMM28 (Zm00001d022088) with the AP1-FUL clade MADS-box genes from Arabidopsis, rice, sorghum, barley, Brachypodium and maize is shown in FIG. 1b. ZMM28 clusters with and shares 94%, 75%, 69%, and 76% amino acid sequence identity with sorghum Sb02g038780.1, barley AK361063 and AK361227, and rice LOC_Os07g41370.1 (OsMADS18) proteins, respectively.

As used herein "encoding," "encoded," or the like, with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capricolum* (Yamao, et al., (1985) Proc. Natl. Acad. Sci. USA 82:2306-9) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98).

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, California, USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may conduct optimal alignment of sequences for comparison; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, California, GAP, BESTFIT, BLAST, FASTA and TFASTA in the Wisconsin Genetics Software Package®, Version 8 (available from Genetics Computer Group (GCG® programs (Accelrys, Inc., San Diego, CA)). The CLUSTAL program is well described by Higgins and Sharp, (1988) Gene 73:237 44; Higgins and Sharp, (1989) CABIOS 5:151 3; Corpet, et al., (1988) Nucleic Acids Res. 16:10881-90; Huang, et al., (1992) Computer Applications in the Biosciences 8:155-65, and Pearson, et al., (1994) Meth. Mol. Biol. 24:307-31. The preferred program to use for optimal global alignment of multiple sequences is PileUp (Feng and Doolittle, (1987) J. Mol. Evol., 25:351-60 which is similar to the method described by Higgins and Sharp, (1989) CABIOS 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, CURRENT PROTOCOLS IN MOLECULAR BIOLOGY, Chapter 19, Ausubel, et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

Accordingly, in any of the embodiments described herein, the polynucleotide may encode a polypeptide that is at least 80% identical to any one of SEQ ID NOS: 1-10, 12-51. For example, the polynucleotide may encode a polypeptide that is at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, or at least 99% identical to the amino acid sequence of any one of SEQ ID NOS: 1-10, 12-51.

B. Recombinant DNA Construct

Also provided is a recombinant DNA construct comprising any of the polynucleotides described herein. In certain embodiments, the recombinant DNA construct further comprises at least one regulatory element. In certain embodiments, the at least one regulatory element of the recombinant DNA construct comprises a promoter. In certain embodiments, the promoter is a heterologous promoter.

As used herein, a "recombinant DNA construct" comprises two or more operably linked DNA segments, preferably DNA segments that are not operably linked in nature (i.e., heterologous). Non-limiting examples of recombinant DNA constructs include a polynucleotide of interest operably linked to heterologous sequences, also referred to as "regulatory elements," which aid in the expression, autologous replication, and/or genomic insertion of the sequence of interest. Such regulatory elements include, for example, promoters, termination sequences, enhancers, etc., or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

The polynucleotides described herein can be provided in expression cassettes for expression in a plant of interest or any organism of interest. The cassette can include 5' and 3' regulatory sequences operably linked to a polynucleotide. "Operably linked" is intended to mean a functional linkage between two or more elements. For, example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (e.g., a promoter), a polynucleotide, and a transcriptional and translational termination region (e.g., termination region) functional in plants. The regulatory regions (e.g., promoters, transcriptional regulatory regions, and translational termination regions) and/or the polynucleotide may be native/analogous to the host cell or to each other. Alternatively, the regulatory regions and/or the polynucleotide may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide that is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region, with the plant host, or may be derived from another source (i.e., foreign or heterologous) than the promoter, the polynucleotide, the plant host, or any combination thereof.

The expression cassette may additionally contain a 5' leader sequences. Such leader sequences can act to enhance translation. Translation leaders are known in the art and include viral translational leader sequences.

In preparing the expression cassette, the various DNA fragments may be manipulated, to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

As used herein "promoter" refers to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such Agrobacterium or Rhizobium. Certain types of promoters preferentially initiate transcription in certain tissues, such as leaves, roots, seeds, fibers, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026); ZmGOS2 (U.S. Pat. No. 6,504,083), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Also contemplated are synthetic promoters which include a combination of one or more heterologous regulatory elements.

C. Plants and Plant Cells

Provided are plants, plant cells, plant parts, seed, and grain comprising a polynucleotide sequence described herein or a recombinant DNA construct described herein, so that the plants, plant cells, plant parts, seed, and/or grain have increased expression of a polypeptide. In certain embodiments, the plants, plant cells, plant parts, seeds, and/or grain have stably incorporated an exogenous polynucleotide described herein into its genome. In certain embodiments, the plants, plant cells, plant parts, seeds, and/or grain can comprise multiple polynucleotides (i.e., at least 1, 2, 3, 4, 5, 6 or more).

In specific embodiments, the polynucleotide(s) in the plants, plant cells, plant parts, seeds, and/or grain are operably linked to a heterologous regulatory element, such as, but not limited to, a constitutive promoter, a tissue-preferred promoter, or a synthetic promoter for expression in plants or a constitutive enhancer. For example, in certain embodiments the heterologous regulatory element is the maize GOS2 promoter.

Also provided herein are plants, plant cells, plant parts, seeds, and grain comprising an introduced genetic modification at a genomic locus that encodes a polypeptide comprising an amino acid sequence that is at least 80% identical to an amino acid sequence selected from the group consisting of SEQ ID NOS: 1-10, 12-51.

In certain embodiments, the genetic modification increases the activity of the protein. In certain embodiments, the genetic modification increases the level of the protein. In certain embodiments, the genetic modification increases both the level and activity of the protein.

A "genomic locus" as used herein, generally refers to the location on a chromosome of the plant where a gene, such as a polynucleotide encoding a polypeptide, is found. As used herein, "gene" includes a nucleic acid fragment that expresses a functional molecule such as, but not limited to, a specific protein coding sequence and regulatory elements, such as those preceding (5' non-coding sequences) and following (3' non-coding sequences) the coding sequence.

A "regulatory element" generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located.

An "enhancer" element is any nucleic acid molecule that increases transcription of a nucleic acid molecule when functionally linked to a promoter regardless of its relative position.

A "repressor" (also sometimes called herein silencer) is defined as any nucleic acid molecule which inhibits the transcription when functionally linked to a promoter regardless of relative position.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene but is not necessarily a part of the sequence that encodes the final gene product.

The 5' untranslated region (5'UTR) (also known as a translational leader sequence or leader RNA) is the region of an mRNA that is directly upstream from the initiation codon. This region is involved in the regulation of translation of a transcript by differing mechanisms in viruses, prokaryotes and eukaryotes.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Genetic modification," "DNA modification," and the like refers to a site-specific modification that alters or changes the nucleotide sequence at a specific genomic locus of the plant. The genetic modification of the compositions and methods described herein may be any modification known in the art such as, for example, insertion, deletion, single nucleotide polymorphism (SNP), and or a polynucleotide modification. Additionally, the targeted DNA modification in the genomic locus may be located anywhere in the genomic locus, such as, for example, a coding region of the encoded polypeptide (e.g., exon), a non-coding region (e.g., intron), a regulatory element, or untranslated region.

As used herein, a "targeted" genetic modification or "targeted" DNA modification, refers to the direct manipulation of an organism's genes. The targeted modification may be introduced using any technique known in the art, such as, for example, plant breeding, genome editing, or single locus conversion.

The type and location of the DNA modification of the polynucleotide is not particularly limited so long as the DNA modification results in increased expression and/or activity of the protein encoded by the corresponding polynucleotide.

In certain embodiments, the plant, plant cells, plant parts, seeds, and/or grain comprise one or more nucleotide modifications present within (a) the coding region; (b) non-coding region; (c) regulatory sequence; (d) untranslated region, or (e) any combination of (a)-(d) of an endogenous polynucleotide encoding a polypeptide.

In certain embodiments the DNA modification is an insertion of one or more nucleotides, preferably contiguous, in the genomic locus. For example, the insertion of an expression modulating element (EME), such as an EME described in PCT/US2018/025446, in operable linkage with the gene of interest described herein. In certain embodiments, the targeted DNA modification may be the replacement of an endogenous promoter with another promoter known in the art to have higher expression, such as, for example, the maize GOS2 promoter. In certain embodiments, the targeted DNA modification may be the insertion of a promoter known in the art to have higher expression, such as, for example, the maize GOS2 promoter, into the 5'UTR so that expression of the endogenous polypeptide is controlled by the inserted promoter. In certain embodiments, the DNA modification is a modification to optimize Kozak context to increase expression. In certain embodiments, the DNA modification is a polynucleotide modification or SNP at a site that regulates the stability of the expressed protein.

As used herein "increased," "increase," or the like refers to any detectable increase in an experimental group (e.g., plant with a DNA modification described herein) as compared to a control group (e.g., wild-type plant that does not comprise the DNA modification). Accordingly, increased expression of a protein comprises any detectable increase in the total level of the protein in a sample and can be determined using routine methods in the art such as, for example, Western blotting and ELISA.

In certain embodiments, the genomic locus has more than one (e.g., 2, 3, 4, 5, 6, 7, 8, 9, or 10) DNA modification. For example, the translated region and a regulatory element of a genomic locus may each comprise a targeted DNA modification. In certain embodiments, more than one genomic locus of the plant may comprise a DNA modification.

The DNA modification of the genomic locus may be done using any genome modification technique known in the art or described herein. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In certain embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

The polynucleotides or recombinant DNA constructs disclosed herein may be used for transformation of any plant species, including, but not limited to, monocots and dicots. Additionally, the genetic modifications described herein may be used to modify any plant species, including, but not limited to, monocots and dicots.

In specific embodiments, plants of the present disclosure are crop plants (for example, corn, alfalfa, sunflower, Brassica, soybean, cotton, safflower, peanut, sorghum, wheat, millet, tobacco, etc.). In other embodiments, corn and soybean plants are optimal, and in yet other embodiments corn plants are optimal.

Other plants of interest include, for example, grain plants that provide seeds of interest, oil-seed plants, and leguminous plants. Seeds of interest include, for example, grain seeds, such as corn, wheat, barley, rice, sorghum, rye, etc. Oil-seed plants include, for example, cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea.

For example, in certain embodiments, maize plants are provided that comprise, in their genome, a recombinant DNA construct comprising a polynucleotide that encodes a polypeptide comprising an amino acid sequence that is at least 80% identical to any one of SEQ ID NOS: 1-10, 12-51. In certain embodiments, the polypeptide comprising an amino acid sequence that is at least 80% identical to the amino acid sequence of any one of SEQ ID NOS: 1-10, 12-51. In certain embodiments, the polypeptide comprising an amino acid sequence that is at least 80% identical to the amino acid sequence of any one of SEQ ID NOS: 1-10, 12-51.

In other embodiments, maize plants are provided that comprise a genetic modification at a genomic locus that encodes a polypeptide comprising an amino acid sequence that is at least 80% identical to the amino acid sequence of any one of SEQ ID NOS: 1-10, 12-51. In certain embodiments, the polypeptide comprising an amino acid sequence that is at least 80% identical to the amino acid sequence of any one of SEQ ID NOS: 1-10, 12-51. In certain embodiments, the polypeptide comprising an amino acid sequence that is at least 80% identical to the amino acid sequence of any one of SEQ ID NOS: 1-10, 12-51.

D. Stacking Other Traits of Interest

In some embodiments, the polynucleotides disclosed herein are engineered into a molecular stack. Thus, the various host cells, plants, plant cells, plant parts, seeds, and/or grain disclosed herein can further comprise one or more traits of interest. In certain embodiments, the host cell, plant, plant part, plant cell, seed, and/or grain is stacked with any combination of polynucleotide sequences of interest in order to create plants with a desired combination of traits. As used herein, the term "stacked" refers to having multiple traits present in the same plant or organism of interest. For example, "stacked traits" may comprise a molecular stack where the sequences are physically adjacent to each other. A trait, as used herein, refers to the phenotype derived from a particular sequence or groups of sequences. In one embodiment, the molecular stack comprises at least one polynucleotide that confers tolerance to glyphosate. Polynucleotides that confer glyphosate tolerance are known in the art.

In certain embodiments, the molecular stack comprises at least one polynucleotide that confers tolerance to glyphosate and at least one additional polynucleotide that confers tolerance to a second herbicide.

In certain embodiments, the plant, plant cell, seed, and/or grain having an inventive polynucleotide sequence may be stacked with, for example, one or more sequences that confer tolerance to: an ALS inhibitor; an HPPD inhibitor; 2,4-D; other phenoxy auxin herbicides; aryloxyphenoxypropionate herbicides; dicamba; glufosinate herbicides; herbicides which target the protox enzyme (also referred to as "protox inhibitors").

The plant, plant cell, plant part, seed, and/or grain having an inventive polynucleotide sequence can also be combined with at least one other trait to produce plants that further comprise a variety of desired trait combinations. For instance, the plant, plant cell, plant part, seed, and/or grain having an inventive polynucleotide sequence may be stacked with polynucleotides encoding polypeptides having pesticidal and/or insecticidal activity, or a plant, plant cell, plant part, seed, and/or grain having an inventive polynucleotide sequence may be combined with a plant disease resistance gene.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference. Any plant having an inventive polynucleotide sequence disclosed herein can be used to make a food or a feed product. Such methods comprise obtaining a plant, explant, seed, plant cell, or cell comprising the polynucleotide sequence and processing the plant, explant, seed, plant cell, or cell to produce a food or feed product.

II. Methods of Use

A. Methods for Increasing Yield, and/or Increasing the Activity of Polynucleotides in a Plant Provided are methods for increasing yield in a plant, modifying flowering time of a plant, and/or increasing the activity of one or more polynucleotides disclosed herein in a plant comprising introducing into a plant, plant cell, plant part, seed, and/or grain a recombinant DNA construct comprising any of the inventive polynucleotides described herein, whereby the polypeptide is expressed in the plant. Also provided are methods for increasing yield in a plant, modifying flowering time of a plant, and/or increasing the activity in a plant comprising introducing a genetic modification at a genomic locus of a plant that encodes a polypeptide comprising an amino acid sequence that is at least 80%-99% or 100% identical to the amino acid sequence set for in any one of SEQ ID NOS: 1-10, 12-51.

The plant for use in the inventive methods can be any plant species described herein. In certain embodiments, the plant is a grain plant, an oil-seed plant, or leguminous plant. In certain embodiments, the plant is a grain plant such as maize.

As used herein, "yield" refers to the amount of agricultural production harvested per unit of land and may include reference to bushels per acre of a crop at harvest, as adjusted for grain moisture (e.g., typically 15% for maize). Grain moisture is measured in the grain at harvest. The adjusted test weight of grain is determined to be the weight in pounds per bushel, adjusted for grain moisture level at harvest.

In certain embodiments yield is measured in plants grown under optimal growth conditions. As used herein, "optimal conditions" refers to plants that are grown under well-watered or non-drought conditions. In certain embodiments, optimal growth conditions are determined based on the yield of the wild-type control plants in the experiment. As used herein, plants are considered to be grown under optimal conditions when the wild-type plant provides at least 75% of the predicted grain yield.

As used herein, "modifying flowering time" refers to a change in the number of days or growth heat units required for a plant to flower. In certain embodiments, the flowering time of the plant is delayed upon increased expression of the polypeptide. Also contemplated are embodiments in which flowering time is decreased (i.e., less days or growth heat units required for a plant to flower) upon decreased expression of the polypeptide.

As used herein, increase in photosynthetic activity, refers to any detectable increase in the functional activity of the protein compared to a suitable control. The functional activity may be any known biological property of one or more of the polypeptides disclosed herein and includes, for example, increased formation of protein complexes, modulation of biochemical pathways, and/or increased grain yield.

Various methods can be used to introduce a sequence of interest into a plant, plant part, plant cell, seed, and/or grain. "Introducing" is intended to mean presenting to the plant, plant cell, seed, and/or grain the inventive polynucleotide or resulting polypeptide in such a manner that the sequence gains access to the interior of a cell of the plant. The methods of the disclosure do not depend on a particular method for introducing a sequence into a plant, plant cell, seed, and/or grain, only that the polynucleotide or polypeptide gains access to the interior of at least one cell of the plant.

"Stable transformation" is intended to mean that the polynucleotide introduced into a plant integrates into the genome of the plant of interest and is capable of being inherited by the progeny thereof. "Transient transformation" is intended to mean that a polynucleotide is introduced into the plant of interest and does not integrate into the genome of the plant or organism or a polypeptide is introduced into a plant or organism.

Transformation protocols as well as protocols for introducing polypeptides or polynucleotide sequences into plants may vary depending on the type of plant or plant cell, i.e., monocot or dicot, targeted for transformation.

In specific embodiments, the polynucleotide sequences disclosed herein can be provided to a plant using a variety of transient transformation methods. Such transient transformation methods include, but are not limited to, the introduction of the encoded protein directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference.

In other embodiments, the inventive polynucleotides disclosed herein may be introduced into plants by contacting plants with a virus or viral nucleic acids. Generally, such methods involve incorporating a nucleotide construct of the disclosure within a DNA or RNA molecule. It is recognized that the inventive polynucleotide sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316, 931, and Porta et al. (1996) *Molecular Biotechnology* 5:209-221; herein incorporated by reference.

Various methods can be used to introduce a genetic modification at a genomic locus that encodes and polypeptide into the plant, plant part, plant cell, seed, and/or grain. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In some embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 Nature Methods Vol. 10: 957-963.) The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to, transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

In addition to modification by a double strand break technology, modification of one or more bases without such double strand break are achieved using base editing technology, see e.g., Gaudelli et al., (2017) Programmable base editing of A*T to G*C in genomic DNA without DNA cleavage. Nature 551(7681):464-471; Komor et al., (2016) Programmable editing of a target base in genomic DNA without double-stranded DNA cleavage, Nature 533(7603): 420-4.

These fusions contain dCas9 or Cas9 nickase and a suitable deaminase, and they can convert e.g., cytosine to uracil without inducing double-strand break of the target DNA. Uracil is then converted to thymine through DNA replication or repair. Improved base editors that have targeting flexibility and specificity are used to edit endogenous locus to create target variations and improve grain yield. Similarly, adenine base editors enable adenine to inosine change, which is then converted to guanine through repair or replication. Thus, targeted base changes i.e., C•G to T•A conversion and A•T to G•C conversion at one more locations made using appropriate site-specific base editors.

In an embodiment, base editing is a genome editing method that enables direct conversion of one base pair to another at a target genomic locus without requiring double-stranded DNA breaks (DSBs), homology-directed repair (HDR) processes, or external donor DNA templates. In an embodiment, base editors include (i) a catalytically impaired CRISPR—Cas9 mutant that are mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; and (iv) nickase activity to cleave the non-edited DNA strand, followed by cellular DNA repair processes to replace the G-containing DNA strand.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as Fokl. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

The terms "target site", "target sequence", "target site sequence," target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide polynucleotide/Cas endonuclease complex to a unique DNA target site.

The terms "knock-out", "gene knock-out" and "genetic knock-out" are used interchangeably herein. A knock-out represents a DNA sequence of a cell that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

The guide polynucleotide/Cas endonuclease system can be used in combination with a co-delivered polynucleotide modification template to allow for editing (modification) of a genomic nucleotide sequence of interest. (See also U.S. Patent Application US 2015-0082478 A1, published on Mar. 19, 2015 and WO2015/026886 A1, published on Feb. 26, 2015, both are hereby incorporated in its entirety by reference.)

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (by HR, wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

The following are examples of specific embodiments of some aspects of the invention. The examples are offered for illustrative purposes only and are not intended to limit the scope of the invention claimed, in any way.

Example 1

Increased and Extended Expression of OsMADS18 Enhances Maize Grain Yield

This example demonstrates that increased and extended expression of a rice MADS transcription factor OsMADS18 (SEQ ID NO: 1) under ZmGOS2 promoter in maize increased grain yield under field conditions. Recombinant expression of OsMADS18 DNA with Zm-Gos2 promoter in maize enhances grain yield in field yield efficacy trials under normal growth conditions. As shown in FIG. 1, nine independent transgenic events had increased yield (p<0.1) in broad acre yield testing across 8 locations when compared to the control that did not have the recombinant OsMADS18. The yield of the events ranges from about 5.7 bushel/acre to about 10.4 bushels/acre higher than non-transgenic controls.

As demonstrated, nine transgenic maize events of Os-MADS18 demonstrated improved yield across multiple locations yield testing (FIG. 1). Values plotted are bushel/acre yield increase of transgenic events over controls. *indicates P<0.1. Base yield (yield of controls) was 184 bushels/acre. Data are shown with BLUP analysis across 8 locations.

Therefore, this Example demonstrates that OsMADS18, an ortholog of maize MADS box protein ZMM28 and exhibiting about 76% amino acid identity across the full-length of the maize MADS box ortholog, surprisingly exhibited increased grain yield under field growth conditions in maize, when its expression level was increased under a moderately constitutive promoter compared to control maize plants lacking such increased and extended expression of OsMADS18.

Example 2

Increased and Extended Expression of SbMADS28 Enhances Maize Grain Yield

Transgenic expression of Sb-MADS28 genomic DNA with Zm-Gos2 promoter in maize enhances grain yield in field yield efficacy trials. As shown in FIG. 2, four transgenic events demonstrated positive yield efficacy. Of which, one event showed significant yield increase, 4 bushels/acre at p<0.1, under low nitrogen yield testing across two locations, and three events showed significant yield increase in normal nitrogen yield testing conditions. The 3 events yielded 6 bushel/acre, 7 bushel/acre and 8 bushel/acre (p<0.1) more than non-transgenic controls under normal nitrogen conditions, respectively.

Four transgenic maize events of SB-MADS28 demonstrate improved yield across multiple locations yield testing. Values plotted are bushel/acre yield increase of transgenic events over controls. *indicates P<0.1. Base yield (yield of controls) was 142 bushels/acre in low N condition and 172 bushels/acre under normal nitrogen condition. Data are shown with BLUP analysis.

Therefore, this Example demonstrates that SbMADS28, an ortholog of maize MADS box protein ZMM28 and exhibiting about 94% amino acid identity to the full-length maize protein, surprisingly exhibited increased grain yield under field growth conditions in maize, when its expression level was increased under a moderately constitutive promoter, compared to control maize plants that did not have such increased expression of SbMADS28 protein.

Example 3

Analysis of Increased Expression of Various MADS Box Proteins on Maize Yield

This example demonstrates the analysis of increasing expression of various monocot MADS box proteins on maize yield. Similar to the analysis described in Example 1 and 2, other monocot orthologs were used to evaluate the effect on maize yield by different promoters. Yield results are presented in Table 2. The field testing results are based on one year of testing.

TABLE 2

Analysis of Monocot Crop MADS box polypeptides

| Entry Number | Type of promoter | Promoter | Gene of Interest | Overall yield signal |
|---|---|---|---|---|
| 43034 | weak constitutive | ZM-GOS2 | OS-MADS GENOMIC | POSITIVE |
| 43053 | weak constitutive | ZM-GOS2 | SB-MADS28 (genomic) | POSITIVE |
| 44759 | weak constitutive | ZM-GOS2 | ZM-ZMM28 (genomic) | NEGATIVE |
| 53759 | weak constitutive | ZM-GOS2 | ZM-ZMM28 (ALT1) | NEUTRAL |
| 67284 | root preferred | ZM-RTM2 PRO | ZM-MADS27 (MOD) | NEUTRAL |
| 70655 | root preferred | ZM-RTM2 PRO | ZM-ANR1 | NEGATIVE |
| 76135 | native | ZM-ZMM28 | ZM-ZMM28 (genomic) | NEUTRAL |
| 77638 | weak constitutive | ZM-GOS2 | OS-MADS BOX GENOMIC (ALT1) | NEUTRAL |
| 77639 | weak constitutive | ZM-GOS2 | OS-MADS BOX GENOMIC (ALT2) | NEUTRAL |
| 77640 | weak constitutive | ZM-GOS2 | OS-MADS BOX GENOMIC (ALT2) | NA |
| 77641 | weak constitutive | ZM-GOS2 | OS-MADS BOX GENOMIC (ALT4) | NEUTRAL |

As shown in Table 2, several monocot crop MADS box protein that are orthologs of ZmM28 were evaluated and those leads that showed positive/neutral/negative yield signal based on one year of field tests were indicated. Different promoters or regulatory elements such expression strength (magnitude) or specificity (e.g., tissue preferred) can be further evaluated and yield increase purposes and tested under various stress environments, such as drought and/or low nitrogen growing conditions. Distant orthologs or proteins having certain structural similarity to ZmM28 were evaluated from Dennstaedtia punctilobula, Artemisia tridentate, Chlorophytum comosum "Variegatum", Eschscholzia california, Lamium amplexicule, Delosperma nubigenum, Peperomia caperata, Triglochin maritima and the overall maize yield signal was either negative or neutral when compared to a wild type control in limited yield trials under a moderatively constitutive promoter.

Terms used in the claims and specification are defined as set forth below unless otherwise specified. It must be noted that, as used in the specification and the appended claims, the singular forms "a," "an" and "the" include plural referents unless the context clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

We claim:

1. A polynucleotide comprising a targeted genetic modification at an endogenous genomic locus encoding a polypeptide comprising an amino acid sequence that is at least 98% identical to SEQ ID NO: 12, wherein the targeted genetic modification increases the expression level and/or activity of the encoded polypeptide thereby resulting in an increased photosynthetic activity of the maize plant cell.

2. The polynucleotide of claim 1, wherein the polynucleotide encodes a polypeptide comprising an amino acid sequence that is at least 99% identical to SEQ ID NO: 12.

3. A recombinant DNA construct comprising the polynucleotide of claim 1 operably linked to a regulatory element.

4. The recombinant DNA construct of claim 3, wherein the regulatory element is a heterologous promoter.

5. A plant cell comprising the polynucleotide of claim 1.

6. The plant cell of claim 5, wherein the plant cell is from a monocot plant.

7. The plant cell of claim 6, wherein the monocot plant is maize.

8. A maize plant cell comprising a targeted genetic modification at an endogenous genomic locus that encodes a polypeptide comprising an amino acid sequence that is at least 98% identical to amino acid sequence SEQ ID NO:12, wherein the targeted genetic modification increases the expression level and/or activity of the encoded polypeptide thereby resulting in an increased photosynthetic activity of the maize plant cell.

9. The plant cell of claim 8, wherein the targeted genetic modification is selected from the group consisting of an insertion, deletion, single nucleotide polymorphism (SNP), and a polynucleotide modification.

10. The plant cell of claim 8, wherein the targeted genetic modification is present in (a) the coding region; (b) a non-coding region; (c) a regulatory sequence; (d) an untranslated region; or (e) any combination of (a)-(d) of the genomic locus that encodes the polypeptide.

11. A method for increasing grain or seed or biomass yield in a plant, the method comprising:
   a. expressing in a regenerable plant cell a recombinant DNA construct comprising a regulatory element operably linked to a polynucleotide comprising a targeted genetic modification at an endogenous genomic locus encoding a polypeptide comprising an amino acid sequence that is at least 98% identical to SEQ ID NO: 12; and
   b. generating the plant, wherein the plant comprises in its genome the recombinant DNA construct.

12. The method of claim 11, wherein the regulatory element is a heterologous promoter.

13. The method of claim 11, wherein the plant cell is from a monocot plant.

14. The method of claim 13, wherein the monocot plant is maize.

* * * * *

SEQUENCE LISTING

```
<160> NUMBER OF SEQ ID NOS: 52

<210> SEQ ID NO 1
<211> LENGTH: 249
<212> TYPE: PRT
<213> ORGANISM: Oryza sativa

<400> SEQUENCE: 1

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Asp Val Ala Leu Ile Val Phe
```

```
                35                  40                  45
Ser Thr Lys Gly Lys Leu Tyr Glu Phe Ser His Ser Ser Met Glu
 50                  55                  60

Gly Ile Leu Glu Arg Tyr Gln Arg Tyr Ser Phe Asp Glu Arg Ala Val
 65                  70                  75                  80

Leu Glu Pro Asn Thr Glu Asp Gln Glu Asn Trp Gly Asp Glu Tyr Gly
                 85                  90                  95

Ile Leu Lys Ser Lys Leu Asp Ala Leu Gln Lys Ser Gln Arg Gln Leu
                100                 105                 110

Leu Gly Glu Gln Leu Asp Thr Leu Thr Ile Lys Glu Leu Gln Gln Leu
                115                 120                 125

Glu His Gln Leu Glu Tyr Ser Leu Lys His Ile Arg Ser Lys Lys Asn
                130                 135                 140

Gln Leu Leu Phe Glu Ser Ile Ser Glu Leu Gln Lys Lys Glu Lys Ser
145                 150                 155                 160

Leu Lys Asn Gln Asn Asn Val Leu Gln Lys Leu Met Glu Thr Glu Lys
                165                 170                 175

Glu Lys Asn Asn Ala Ile Ile Asn Thr Asn Arg Glu Glu Gln Asn Gly
                180                 185                 190

Ala Thr Pro Ser Thr Ser Ser Pro Thr Pro Val Thr Ala Pro Asp Pro
                195                 200                 205

Ile Pro Thr Thr Asn Asn Ser Gln Ser Gln Pro Arg Gly Ser Gly Glu
                210                 215                 220

Ser Glu Ala Gln Pro Ser Pro Ala Gln Ala Gly Asn Ser Lys Leu Pro
225                 230                 235                 240

Pro Trp Met Leu Arg Thr Ser His Thr
                245

<210> SEQ ID NO 2
<211> LENGTH: 253
<212> TYPE: PRT
<213> ORGANISM: Sorghum bicolor

<400> SEQUENCE: 2

Met Gly Arg Gly Pro Val Gln Leu Arg Arg Ile Glu Asn Lys Ile Asn
 1                   5                  10                  15

Arg Gln Val Thr Phe Ser Lys Arg Arg Asn Gly Leu Leu Lys Lys Ala
                 20                  25                  30

His Glu Ile Ser Val Leu Cys Asp Ala Glu Val Ala Leu Ile Val Phe
                 35                  40                  45

Ser Thr Lys Gly Lys Leu Tyr Glu Tyr Ser Ser His Ser Ser Met Glu
 50                  55                  60

Gly Ile Leu Glu Arg Tyr Gln Arg Tyr Ser Phe Glu Glu Arg Ala Val
 65                  70                  75                  80

Leu Asp Pro Thr Ile Glu Asp Gln Ala Asn Trp Gly Asp Glu Tyr Val
                 85                  90                  95

Arg Leu Lys Ser Lys Leu Asp Ala Leu Gln Lys Ser Gln Arg Gln Leu
                100                 105                 110

Leu Gly Glu Gln Leu Asp Ser Leu Thr Ile Lys Glu Leu Gln Gln Leu
                115                 120                 125

Glu Gln Gln Leu Asp Ser Ser Leu Lys His Ile Arg Ser Arg Lys Asn
                130                 135                 140

Gln Leu Met Phe Asp Ser Ile Ser Glu Leu Gln Lys Lys Glu Lys Ala
145                 150                 155                 160
```

-continued

```
Leu Thr Asp Gln Asn Gly Val Leu Gln Lys Leu Met Glu Ala Glu Lys
            165                 170                 175

Glu Lys Asn Asn Ala Leu Met Asn Ala His Leu Arg Glu Gln Pro Asn
        180                 185                 190

Gly Ala Ser Thr Ser Ser Pro Ser Leu Ser Pro Val Val Pro Asp
    195                 200                 205

Ser Met Pro Thr Leu Asn Ile Gly Pro Cys Gln Pro Arg Gly Ala Gly
210                 215                 220

Lys Ser Glu Pro Gly Pro Ser Pro Ala Pro Gln Ala Asn Ser Gly
225                 230                 235                 240

Asn Leu Pro Pro Trp Met Leu Arg Thr Val Ser Asn Arg
                245                 250
```

<210> SEQ ID NO 3
<211> LENGTH: 251
<212> TYPE: PRT
<213> ORGANISM: Zea mays

<400> SEQUENCE: 3

```
Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser His Ser Ser Met Glu
    50                  55                  60

Gly Ile Leu Glu Arg Tyr Gln Arg Tyr Ser Phe Glu Glu Arg Ala Val
65                  70                  75                  80

Leu Glu Pro Ser Ile Glu Asp Gln Ala Asn Trp Gly Asp Glu Tyr Val
                85                  90                  95

Arg Leu Lys Ser Lys Leu Asp Ala Leu Gln Lys Ser Gln Arg Gln Leu
            100                 105                 110

Leu Gly Glu Gln Leu Ser Ser Leu Thr Ile Lys Glu Leu Gln Gln Leu
        115                 120                 125

Glu Gln Gln Leu Asp Ser Ser Leu Lys His Ile Arg Ser Arg Lys Asn
    130                 135                 140

Gln Leu Met Phe Asp Ser Ile Ser Ala Leu Gln Lys Lys Glu Lys Ala
145                 150                 155                 160

Leu Thr Asp Gln Asn Gly Val Leu Gln Lys Phe Met Glu Ala Glu Lys
                165                 170                 175

Glu Lys Asn Lys Ala Leu Met Asn Ala Gln Leu Arg Glu Gln Gln Asn
            180                 185                 190

Gly Ala Ser Thr Ser Ser Pro Ser Leu Ser Pro Ile Val Pro Asp
        195                 200                 205

Ser Met Pro Thr Leu Asn Ile Gly Pro Cys Gln His Arg Gly Ala Ser
210                 215                 220

Glu Ser Glu Ser Glu Pro Ser Pro Ala Pro Ala Gln Ala Asn Arg Gly
225                 230                 235                 240

Asn Leu Pro Pro Trp Met Leu Arg Thr Val Lys
                245                 250
```

<210> SEQ ID NO 4
<211> LENGTH: 248
<212> TYPE: PRT
<213> ORGANISM: Zea mays

```
<400> SEQUENCE: 4

Met Gly Arg Gly Lys Val Glu Leu Lys Arg Ile Glu Asn Lys Ile Ser
1               5                   10                  15

Arg Gln Val Thr Phe Ala Lys Arg Arg Asn Gly Leu Leu Lys Lys Ala
            20                  25                  30

Tyr Glu Leu Ser Leu Leu Cys Asp Ala Glu Val Ala Leu Ile Ile Phe
        35                  40                  45

Ser Gly Arg Gly Arg Leu Phe Glu Phe Ser Ser Ser Trp Tyr Asp
    50                  55                  60

Ala Arg Ala Leu Arg Met Tyr Lys Thr Leu Glu Arg Tyr Arg Ser Ser
65                  70                  75                  80

Asn Tyr Ser Gln Glu Val Lys Thr Pro Leu Asp Thr Glu Ile Lys Tyr
                85                  90                  95

Gln Asp Tyr Leu Lys Leu Arg Thr Arg Val Glu Phe Leu Gln Thr Thr
            100                 105                 110

Gln Arg Asn Ile Leu Gly Glu Asp Leu Gly Pro Leu Ser Met Lys Glu
        115                 120                 125

Leu Glu Gln Leu Glu Asp Gln Ile Glu Ile Ser Leu Lys His Ile Ser
130                 135                 140

Ser Arg Lys Asn Gln Met Leu Leu Asp Gln Leu Phe Asp Leu Lys Ser
145                 150                 155                 160

Lys Glu Gln Glu Leu Leu Asp Leu Asn Lys Asp Leu Arg Lys Gln Leu
                165                 170                 175

Gln Glu Thr Arg Pro Glu Asn Ala Leu Arg Val Ser Trp Glu Glu Gly
            180                 185                 190

Gly His Ser Gly Ala Ser Gly Asn Val Leu Asp Pro Tyr Gln Gly Leu
        195                 200                 205

Leu Gln His Leu Asp Asn Asp Pro Ser Leu Gln Phe Gly Tyr His His
210                 215                 220

Gln Ala Tyr Met Asp Gln Leu Asn Asn Glu Asp Leu Val Asp Pro Asn
225                 230                 235                 240

Glu His Gly Arg Ser Gly Trp Ile
                245

<210> SEQ ID NO 5
<211> LENGTH: 240
<212> TYPE: PRT
<213> ORGANISM: Zea mays

<400> SEQUENCE: 5

Met Gly Arg Gly Lys Ile Val Ile Arg Arg Ile Asp Asn Ser Thr Ser
1               5                   10                  15

Arg Gln Val Thr Phe Ser Lys Arg Arg Asn Gly Ile Phe Lys Lys Ala
            20                  25                  30

Lys Glu Leu Ala Ile Leu Cys Asp Ala Glu Val Gly Leu Val Ile Phe
        35                  40                  45

Ser Ser Thr Gly Arg Leu Tyr Glu Tyr Ser Ser Thr Ser Met Lys Ser
    50                  55                  60

Val Ile Asp Arg Tyr Gly Lys Ala Lys Glu Glu Gln Gln Val Val Ala
65                  70                  75                  80

Asn Pro Asn Ser Glu Leu Lys Phe Trp Gln Arg Glu Ala Ala Ser Leu
                85                  90                  95

Arg Gln Gln Leu His Asn Leu Gln Glu Asn Tyr Arg Gln Leu Thr Gly
            100                 105                 110
```

Asp Asp Leu Ser Gly Leu Asn Val Lys Glu Leu Gln Ser Leu Glu Asn
            115                 120                 125

Gln Leu Glu Thr Ser Leu Arg Gly Val Arg Ala Lys Lys Asp His Leu
    130                 135                 140

Leu Ile Asp Glu Ile His Asp Leu Asn Arg Lys Ala Ser Leu Phe His
145                 150                 155                 160

Gln Glu Asn Thr Asp Leu Tyr Asn Lys Ile Asn Leu Ile Arg Gln Glu
                165                 170                 175

Asn Asp Glu Leu His Lys Lys Ile Tyr Glu Thr Glu Gly Pro Ser Gly
            180                 185                 190

Val Asn Arg Glu Ser Pro Thr Pro Phe Asn Phe Ala Val Val Glu Thr
        195                 200                 205

Arg Asp Val Pro Val Gln Leu Glu Leu Ser Thr Leu Pro Gln Gln Asn
210                 215                 220

Asn Ile Glu Pro Ser Thr Ala Pro Lys Leu Gly Leu Gln Leu Ile Pro
225                 230                 235                 240

<210> SEQ ID NO 6
<211> LENGTH: 250
<212> TYPE: PRT
<213> ORGANISM: Oryza sativa

<400> SEQUENCE: 6

Met Gly Arg Gly Pro Val Gln Leu Arg Arg Ile Glu Asn Lys Ile Asn
1               5                   10                  15

Arg His Val Thr Phe Ser Lys Arg Arg Asn Gly Leu Leu Lys Lys Ala
            20                  25                  30

His Glu Ile Ser Val Leu Cys Asp Ala Asp Val Ala Leu Ile Val Phe
        35                  40                  45

Ser Thr Lys Gly Lys Leu Tyr Glu Phe Ser Ser His Ser Ser Met Glu
    50                  55                  60

Gly Ile Leu Glu Arg Tyr Gln Arg Tyr Ser Phe Asp Glu Arg Ala Val
65                  70                  75                  80

Leu Glu Pro Asn Thr Glu Asp Gln Glu Asn Trp Gly Asp Glu Tyr Gly
                85                  90                  95

Ile Leu Lys Ser Lys Leu Asp Ala Leu Gln Lys Ser Gln Arg Gln Leu
            100                 105                 110

Leu Gly Glu Gln Leu Asp Thr Leu Thr Ile Lys Glu Leu Gln Gln Leu
        115                 120                 125

Glu His Gln Leu Glu Tyr Ser Leu Lys His Ile Arg Ser Lys Lys Asn
    130                 135                 140

Gln Leu Leu Phe Glu Ser Ile Ser Glu Leu Gln Lys Lys Glu Lys Ser
145                 150                 155                 160

Leu Lys Asn Gln Asn Asn Val Leu Gln Lys Leu Met Glu Thr Glu Lys
                165                 170                 175

Glu Lys Asn Asn Ala Ile Ile Asn Thr Asn Arg Glu Glu Gln Asn Gly
            180                 185                 190

Ala Thr Pro Ser Thr Ser Ser Pro Thr Pro Val Thr Ala Pro Asp Pro
        195                 200                 205

Ile Pro Thr Thr Asn Asn Ser Gln Ser Gln Pro Arg Gly Ser Gly Glu
    210                 215                 220

Ser Glu Ala Gln Pro Ser Pro Ala Gln Ala Gly Asn Ser Lys Leu Ile
225                 230                 235                 240

Pro Pro Tyr Met Leu Arg Thr Ser His Thr
                245                 250

<210> SEQ ID NO 7
<211> LENGTH: 250
<212> TYPE: PRT
<213> ORGANISM: Oryza sativa

<400> SEQUENCE: 7

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Asp Val Ala Leu Ile Val Phe
        35                  40                  45

Ser Thr Lys Gly Lys Leu Tyr Glu Phe Ser Ser His Ser Ser Met Glu
    50                  55                  60

Gly Ile Leu Glu Arg Tyr Gln Arg Tyr Ser Phe Asp Glu Arg Ala Val
65                  70                  75                  80

Leu Glu Pro Asn Thr Glu Asp Gln Glu Asn Trp Gly Asp Glu Tyr Gly
                85                  90                  95

Ile Leu Lys Ser Lys Leu Asp Ala Leu Gln Lys Ser Gln Arg Gln Leu
            100                 105                 110

Leu Gly Glu Gln Leu Asp Thr Leu Thr Ile Lys Glu Leu Gln Gln Leu
        115                 120                 125

Glu His Gln Leu Glu Tyr Ser Leu Lys His Ile Arg Ser Lys Lys Asn
    130                 135                 140

Gln Leu Leu Phe Glu Ser Ile Ser Glu Leu Gln Lys Lys Glu Lys Ser
145                 150                 155                 160

Leu Lys Asn Gln Asn Asn Val Leu Gln Lys Leu Met Glu Thr Glu Lys
                165                 170                 175

Glu Lys Asn Asn Ala Ile Ile Asn Thr Asn Arg Glu Glu Gln Asn Gly
            180                 185                 190

Ala Thr Pro Ser Thr Ser Ser Pro Thr Pro Val Thr Ala Pro Asp Pro
        195                 200                 205

Ile Pro Thr Thr Asn Asn Ser Gln Ser Gln Pro Arg Gly Ser Gly Glu
    210                 215                 220

Ser Glu Ala Gln Pro Ser Pro Ala Gln Ala Gly Asn Ser Lys Leu Ile
225                 230                 235                 240

Pro Pro Trp Met Leu Arg Thr Ser His Thr
                245                 250

<210> SEQ ID NO 8
<211> LENGTH: 252
<212> TYPE: PRT
<213> ORGANISM: Oryza sativa

<400> SEQUENCE: 8

Met Gly Arg Gly Pro Val Gln Leu Arg Arg Ile Glu Asn Lys Ile Asn
1               5                   10                  15

Arg His Val Thr Phe Ser Lys Arg Arg Asn Gly Leu Leu Lys Lys Ala
            20                  25                  30

His Glu Ile Ser Val Leu Cys Asp Ala Asp Val Ala Leu Ile Val Phe
        35                  40                  45

Ser Thr Lys Gly Lys Leu Tyr Glu Phe Ser Ser His Ser Ser Met Glu
    50                  55                  60

Gly Ile Leu Glu Arg Tyr Gln Arg Tyr Ser Phe Asp Glu Arg Ala Val

```
65                  70                  75                  80
Leu Glu Pro Asn Thr Glu Asp Gln Glu Asn Trp Gly Asp Glu Tyr Gly
                85                  90                  95

Ile Leu Lys Ser Lys Leu Asp Ala Leu Gln Lys Ser Gln Arg Gln Leu
            100                 105                 110

Leu Gly Glu Gln Leu Asp Thr Leu Thr Ile Lys Glu Leu Gln Gln Leu
        115                 120                 125

Glu His Gln Leu Glu Tyr Ser Leu Lys His Ile Arg Ser Lys Lys Asn
    130                 135                 140

Gln Leu Leu Phe Glu Ser Ile Ser Glu Leu Gln Lys Lys Glu Lys Ser
145                 150                 155                 160

Leu Lys Asn Gln Asn Asn Val Leu Gln Lys Leu Met Glu Thr Glu Lys
                165                 170                 175

Glu Lys Asn Asn Ala Ile Ile Asn Thr Asn Arg Glu Glu Gln Asn Gly
            180                 185                 190

Ala Thr Pro Ser Thr Ser Ser Pro Thr Pro Val Thr Ala Pro Asp Pro
        195                 200                 205

Ile Pro Thr Thr Asn Asn Ser Gln Ser Gln Pro Arg Gly Ser Gly Glu
    210                 215                 220

Ser Glu Ala Gln Pro Ser Pro Ala Gln Ala Gly Asn Ser Lys Leu Ile
225                 230                 235                 240

Pro Pro Pro Pro Trp Met Leu Arg Thr Ser His Thr
                245                 250

<210> SEQ ID NO 9
<211> LENGTH: 252
<212> TYPE: PRT
<213> ORGANISM: Oryza sativa

<400> SEQUENCE: 9

Met Gly Arg Gly Pro Val Gln Leu Arg Arg Ile Glu Asn Lys Ile Asn
1               5                   10                  15

Arg His Val Thr Phe Ser Lys Arg Arg Asn Gly Leu Leu Lys Lys Ala
            20                  25                  30

His Glu Ile Ser Val Leu Cys Asp Ala Asp Val Ala Leu Ile Val Phe
        35                  40                  45

Ser Thr Lys Gly Lys Leu Tyr Glu Phe Ser Ser His Ser Ser Met Glu
    50                  55                  60

Gly Ile Leu Glu Arg Tyr Gln Arg Tyr Ser Phe Asp Glu Arg Ala Val
65                  70                  75                  80

Leu Glu Pro Asn Thr Glu Asp Gln Glu Asn Trp Gly Asp Glu Tyr Gly
                85                  90                  95

Ile Leu Lys Ser Lys Leu Asp Ala Leu Gln Lys Ser Gln Arg Gln Leu
            100                 105                 110

Leu Gly Glu Gln Leu Asp Thr Leu Thr Ile Lys Glu Leu Gln Gln Leu
        115                 120                 125

Glu His Gln Leu Glu Tyr Ser Leu Lys His Ile Arg Ser Lys Lys Asn
    130                 135                 140

Gln Leu Leu Phe Glu Ser Ile Ser Glu Leu Gln Lys Lys Glu Lys Ser
145                 150                 155                 160

Leu Lys Asn Gln Asn Asn Val Leu Gln Lys Leu Met Glu Thr Glu Lys
                165                 170                 175

Glu Lys Asn Asn Ala Ile Ile Asn Thr Asn Arg Glu Glu Gln Asn Gly
            180                 185                 190
```

```
Ala Thr Pro Ser Thr Ser Ser Pro Thr Pro Val Thr Ala Pro Asp Pro
            195                 200                 205

Ile Pro Thr Thr Asn Asn Ser Gln Ser Gln Pro Arg Gly Ser Gly Glu
    210                 215                 220

Ser Glu Ala Gln Pro Ser Pro Ala Gln Ala Gly Asn Ser Lys Leu Ile
225                 230                 235                 240

Pro Phe Pro Phe Trp Met Leu Arg Thr Ser His Thr
                245                 250
```

```
<210> SEQ ID NO 10
<211> LENGTH: 251
<212> TYPE: PRT
<213> ORGANISM: Zea mays

<400> SEQUENCE: 10

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser His Ser Ser Met Glu
    50                  55                  60

Gly Ile Leu Glu Arg Tyr Gln Arg Tyr Ser Phe Glu Glu Arg Ala Val
65                  70                  75                  80

Leu Asn Pro Ser Ile Glu Asp Gln Ala Asn Trp Gly Asp Glu Tyr Val
                85                  90                  95

Arg Leu Lys Ser Lys Leu Asp Ala Leu Gln Lys Ser Gln Arg Gln Leu
            100                 105                 110

Leu Gly Glu Gln Leu Ser Ser Leu Thr Ile Lys Glu Leu Gln Gln Leu
        115                 120                 125

Glu Gln Gln Leu Asp Ser Ser Leu Lys His Ile Arg Ser Arg Lys Asn
    130                 135                 140

Gln Leu Met Phe Asp Ser Ile Ser Ala Leu Gln Lys Lys Glu Lys Ala
145                 150                 155                 160

Leu Thr Asp Gln Asn Gly Val Leu Gln Lys Phe Met Glu Ala Glu Lys
                165                 170                 175

Glu Lys Asn Lys Ala Leu Met Asn Ala Gln Leu Arg Gly Gln Gln Asn
            180                 185                 190

Gly Ala Ser Thr Ser Ser Pro Ser Leu Ser Pro Ile Val Pro Asp
        195                 200                 205

Ser Met Pro Thr Leu Asn Ile Gly Pro Cys Gln Pro Arg Gly Gly Ala
    210                 215                 220

Glu Ser Glu Ser Glu Pro Ser Pro Ala Pro Ala Gln Ala Asn Arg Gly
225                 230                 235                 240

Asn Leu Pro Pro Trp Met Leu Arg Thr Val Lys
                245                 250
```

```
<210> SEQ ID NO 11
<211> LENGTH: 251
<212> TYPE: PRT
<213> ORGANISM: Zea mays

<400> SEQUENCE: 11

Met Gly Arg Gly Pro Val Gln Leu Arg Arg Ile Glu Asn Lys Ile Asn
1               5                   10                  15
```

```
Arg Gln Val Thr Phe Ser Lys Arg Arg Asn Gly Leu Leu Lys Lys Ala
             20                  25                  30

His Glu Ile Ser Val Leu Cys Asp Ala Glu Val Ala Leu Ile Val Phe
         35                  40                  45

Ser Thr Lys Gly Lys Leu Tyr Glu Tyr Ser Ser His Ser Ser Met Glu
 50                  55                  60

Gly Ile Leu Glu Arg Tyr Gln Arg Tyr Ser Phe Glu Glu Arg Ala Val
 65                  70                  75                  80

Leu Asn Pro Ser Ile Glu Asp Gln Ala Asn Trp Gly Asp Glu Tyr Val
                 85                  90                  95

Arg Leu Lys Ser Lys Leu Asp Ala Leu Gln Lys Ser Gln Arg Gln Leu
            100                 105                 110

Leu Gly Glu Gln Leu Ser Ser Leu Thr Ile Lys Glu Leu Gln Gln Leu
        115                 120                 125

Glu Gln Gln Leu Asp Ser Ser Leu Lys His Ile Arg Ser Arg Lys Asn
130                 135                 140

Gln Leu Met Phe Asp Ser Ile Ser Ala Leu Gln Lys Lys Glu Lys Ala
145                 150                 155                 160

Leu Thr Asp Gln Asn Gly Val Leu Gln Lys Phe Met Glu Ala Glu Lys
                165                 170                 175

Glu Lys Asn Lys Ala Leu Met Asn Ala Gln Leu Arg Glu Gln Gln Asn
            180                 185                 190

Gly Ala Ser Thr Ser Ser Pro Ser Leu Ser Pro Pro Ile Val Pro Asp
        195                 200                 205

Ser Met Pro Thr Leu Asn Ile Gly Pro Cys Gln His Arg Gly Ala Ala
210                 215                 220

Glu Ser Glu Ser Glu Pro Ser Pro Ala Pro Ala Gln Ala Asn Arg Gly
225                 230                 235                 240

Asn Leu Pro Pro Trp Met Leu Arg Thr Val Lys
                245                 250

<210> SEQ ID NO 12
<211> LENGTH: 189
<212> TYPE: PRT
<213> ORGANISM: Zea mays

<400> SEQUENCE: 12

Met Glu Gly Ile Leu Glu Arg Tyr Gln Arg Tyr Ser Phe Glu Glu Arg
 1               5                  10                  15

Ala Val Leu Asn Pro Ser Ile Glu Asp Gln Ala Asn Trp Gly Asp Glu
             20                  25                  30

Tyr Val Arg Leu Lys Ser Lys Leu Asp Ala Leu Gln Lys Ser Gln Arg
         35                  40                  45

Gln Leu Leu Gly Glu Gln Leu Ser Ser Leu Thr Ile Lys Glu Leu Gln
 50                  55                  60

Gln Leu Glu Gln Gln Leu Asp Ser Ser Leu Lys His Ile Arg Ser Arg
 65                  70                  75                  80

Lys Asn Gln Leu Met Phe Asp Ser Ile Ser Ala Leu Gln Lys Lys Glu
                 85                  90                  95

Lys Ala Leu Thr Asp Gln Asn Gly Val Leu Gln Lys Phe Met Glu Ala
            100                 105                 110

Glu Lys Glu Lys Asn Lys Ala Leu Met Asn Ala Gln Leu Arg Glu Gln
        115                 120                 125

Gln Asn Gly Ala Ser Thr Ser Ser Pro Ser Leu Ser Pro Pro Ile Val
130                 135                 140
```

```
Pro Asp Ser Met Pro Thr Leu Asn Ile Gly Pro Cys Gln His Arg Gly
145                 150                 155                 160

Ala Ala Glu Ser Glu Ser Pro Ser Pro Ala Pro Ala Gln Ala Asn
            165                 170                 175

Arg Gly Asn Leu Pro Pro Trp Met Leu Arg Thr Val Lys
        180                 185
```

<210> SEQ ID NO 13
<211> LENGTH: 253
<212> TYPE: PRT
<213> ORGANISM: Panicum virgatum

<400> SEQUENCE: 13

```
Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Arg Leu Tyr Glu Tyr Ser His Glu Ser Met Glu
50                  55                  60

Gly Ile Leu Glu Arg Tyr Gln Arg Tyr Ser Phe Glu Glu Arg Ala Val
65                  70                  75                  80

Leu Asp Pro Ser Ile Ala Asp Gln Ala Asn Trp Gly Asp Glu Tyr Gly
                85                  90                  95

Arg Leu Lys Thr Lys Leu Asp Ala Leu Gln Lys Ser Gln Arg Gln Leu
            100                 105                 110

Leu Gly Glu Gln Leu Asp Ser Leu Thr Ile Lys Glu Leu Gln Gln Leu
        115                 120                 125

Glu Gln Gln Leu Asp Ser Ser Leu Lys His Ile Arg Ser Arg Lys Asn
130                 135                 140

Gln Leu Met Phe Tyr Ser Ile Ser Glu Leu Gln Lys Lys Glu Lys Ser
145                 150                 155                 160

Leu Thr Asp Gln Asn Gly Val Leu Gln Lys Leu Met Glu Ala Glu Lys
                165                 170                 175

Glu Lys Asn Asn Ala Leu Met Asn Ala His Leu Arg Glu Gln Gln Asn
            180                 185                 190

Gly Ala Ser Thr Ser Leu Pro Ser Pro Leu Ser Thr Val Pro Asp
        195                 200                 205

Ser Leu Pro Thr Leu Asn Ile Gly Pro Cys Gln Pro Arg Gly Gly Thr
210                 215                 220

Val Gly Glu Ser Glu Pro Glu Pro Ser Pro Ala Gln Val Asn Ser Gly
225                 230                 235                 240

Lys Leu Pro Pro Trp Met Leu Arg Ser Val Ser Asn Arg
                245                 250
```

<210> SEQ ID NO 14
<211> LENGTH: 252
<212> TYPE: PRT
<213> ORGANISM: Setaria italica

<400> SEQUENCE: 14

```
Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30
```

His Glu Ile Ser Val Leu Cys Asp Ala Glu Val Ala Leu Ile Val Phe
            35                  40                  45

Ser Thr Lys Gly Lys Leu Tyr Glu Tyr Ser Ser His Glu Ser Met Glu
 50                  55                  60

Gly Ile Leu Glu Arg Tyr Gln Arg Tyr Ser Phe Glu Glu Arg Ala Val
 65                  70                  75                  80

Leu Asp Pro Asn Ile Gly Asp Gln Ala Asn Trp Gly Asp Glu Tyr Gly
                 85                  90                  95

Arg Leu Lys Ser Lys Leu Asp Ala Leu Gln Lys Ser Gln Arg Gln Leu
            100                 105                 110

Leu Gly Glu Gln Leu Asp Ser Leu Thr Ile Lys Glu Leu His Gln Leu
            115                 120                 125

Glu Gln Gln Leu Asp Ser Ser Leu Lys His Ile Arg Ser Arg Lys Asn
    130                 135                 140

Gln Leu Met Phe Asn Ser Ile Ser Glu Leu Gln Lys Lys Glu Lys Ser
145                 150                 155                 160

Leu Thr Asp Gln Asn Gly Val Leu Gln Lys Leu Met Glu Ala Glu Lys
                165                 170                 175

Glu Lys Asn Asn Ala Leu Met Asn Thr His Leu Arg Glu Gln Gln Asn
            180                 185                 190

Gly Ala Ser Lys Ser Ser Pro Ser Pro Pro Ser Thr Val Pro Asp
            195                 200                 205

Ser Leu Pro Thr Leu Asp Ile Gly Pro Cys Gln Pro Arg Gly Thr Gly
    210                 215                 220

Gly Glu Ser Glu Pro Glu Pro Ile Pro Ala Gln Val Asn Ser Gly Lys
225                 230                 235                 240

Leu Pro Pro Trp Met Leu Arg Ser Val Asn Asn Arg
                245                 250

<210> SEQ ID NO 15
<211> LENGTH: 240
<212> TYPE: PRT
<213> ORGANISM: Dichanthelium oligosanthes

<400> SEQUENCE: 15

Met Gly Arg Gly Pro Val Gln Leu Arg Arg Ile Glu Asn Lys Ile Asn
 1               5                  10                  15

Arg Gln Val Thr Phe Ser Lys Arg Arg Asn Gly Leu Leu Lys Lys Ala
                20                  25                  30

His Glu Ile Ser Val Leu Cys Asp Ala Glu Val Ala Leu Ile Val Phe
            35                  40                  45

Ser Thr Lys Gly Lys Leu Tyr Glu Tyr Ser Ser Asn His Ala Ser Met
 50                  55                  60

Glu Gly Ile Leu Asp Arg Tyr Gln Arg Tyr Ser Phe Glu Glu Arg Ala
 65                  70                  75                  80

Val Leu Asp Pro Asn Ile Glu Asp Gln Ala Asn Trp Gly Asp Glu Tyr
                 85                  90                  95

Gly Arg Leu Lys Ser Lys Leu Glu Ala Leu Gln Lys Ser Gln Arg Gln
            100                 105                 110

Leu Leu Gly Glu Gln Leu Asp Pro Leu Thr Ile Lys Glu Leu Gln Gln
            115                 120                 125

Leu Glu Gln Gln Leu Asp Ser Ser Leu Lys His Ile Arg Ser Arg Lys
    130                 135                 140

Asn Gln Leu Met Phe Asp Ser Ile Ser Glu Leu Gln Lys Lys Leu Val

```
            145                 150                 155                 160
Glu Ala Glu Lys Glu Lys Asn Asn Ala Leu Met Ser Ala His Leu Arg
                165                 170                 175

Glu Gln Arg His Gly Ala Ser Thr Ser Ser Pro Ser Pro Ser Leu Ser
                180                 185                 190

Thr Val Pro Asp Ser Met Pro Ala Leu Asn Ile Gly Pro Ser Gln Pro
                195                 200                 205

Arg Gly Thr Gly Gly Glu Ser Glu Pro Glu Pro Ser Ala Ala Gln Val
                210                 215                 220

Ile Ser Gly Lys Leu Pro Pro Trp Met Leu Arg Ser Val Arg Lys Arg
225                 230                 235                 240

<210> SEQ ID NO 16
<211> LENGTH: 255
<212> TYPE: PRT
<213> ORGANISM: Phyllostachys edulis

<400> SEQUENCE: 16

Met Gly Arg Gly Pro Val Gln Leu Arg Arg Ile Glu Asn Lys Ile Asn
1                   5                   10                  15

Arg Gln Val Thr Phe Ser Lys Arg Arg Asn Gly Leu Leu Lys Lys Ala
                20                  25                  30

His Glu Ile Ser Val Leu Cys Asp Ala Glu Val Ala Leu Ile Val Phe
            35                  40                  45

Ser Thr Lys Gly Lys Leu Tyr Glu Tyr Ser Ser Gln Ala Ser Asn Met
        50                  55                  60

Glu Gly Ile Leu Asp Arg Tyr Gln Arg Tyr Ser Phe Glu Glu Arg Ala
65                  70                  75                  80

Val Leu Asp Pro Asn Ile Gly Asp Gln Ala Asn Trp Gly Asp Glu Tyr
                85                  90                  95

Gly Arg Leu Lys Thr Lys Leu Asp Ala Leu Gln Lys Ser Gln Arg Gln
                100                 105                 110

Leu Leu Gly Glu Gln Leu Asp Ala Leu Thr Ile Lys Glu Leu Gln Gln
            115                 120                 125

Leu Glu Gln Gln Leu Asp Ser Ser Leu Lys His Ile Arg Ser Arg Lys
        130                 135                 140

Lys Gln Leu Leu Phe Glu Ser Ile Ser Glu Leu Gln Lys Lys Glu Lys
145                 150                 155                 160

Ser Leu Thr Asp Gln Asn Asp Leu Leu Gln Lys His Leu Val Glu Leu
                165                 170                 175

Glu Lys Glu Lys Asn Asn Val Leu Leu Asn Thr His Gln Arg Asp Gln
                180                 185                 190

Pro Asn Gly Ala Thr Thr Ser Ser Pro Ser Pro Thr Pro Val Thr Val
            195                 200                 205

Gln Asp Phe Met Pro Thr Leu Asn Ile Gly Pro Tyr Gln Ser Arg Gly
        210                 215                 220

Ala Gly Glu Glu Ser Glu Pro Gln Pro Pro Ala Gln Val Asn Ser
225                 230                 235                 240

Ser Lys Leu Pro Pro Trp Met Leu Pro Thr Val Asn Asn Asn Thr
                245                 250                 255

<210> SEQ ID NO 17
<211> LENGTH: 270
<212> TYPE: PRT
<213> ORGANISM: Brachypodium distachyon
```

<400> SEQUENCE: 17

```
Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser Gln Asp Ser Ser Met
50                  55                  60

Asp Val Ile Leu Glu Arg Tyr Gln Arg Tyr Ser Phe Glu Glu Arg Ala
65                  70                  75                  80

Val Leu Asp Pro Asn Ile Gly Asp Gln Ala Asn Trp Gly Asp Glu Tyr
                85                  90                  95

Gly Arg Leu Lys Ile Lys Leu Asp Ala Leu Gln Lys Ser Gln Arg Gln
            100                 105                 110

Leu Leu Gly Glu Gln Leu Glu Pro Leu Thr Thr Arg Glu Leu Gln Gln
        115                 120                 125

Leu Glu Gln Gln Leu Asp Ser Ser Leu Lys His Ile Arg Ser Arg Lys
130                 135                 140

Asn Gln Leu Leu Phe Asp Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Asn Asn Ala Leu Ser Asn Ile Gln His Arg Glu Gln
            180                 185                 190

Leu Asn Glu Lys Asn Thr Ala Leu Pro Asn Thr His Asp Arg Glu Gln
        195                 200                 205

Gln Asn Gly Ala Thr Thr Ser Ser Pro Ser Pro Thr Pro Leu Thr Val
210                 215                 220

Leu Asp Ser Met Pro Asn Leu Asn Ile Gly Ser His Gln Pro Arg Glu
225                 230                 235                 240

Ala Gly Gly Glu Pro Glu Ser Gln Pro Ser Pro Ala Gln Ala Asn Ser
                245                 250                 255

Gly Lys Leu Pro Pro Trp Met Leu Arg Thr Ile Ser Asn Arg
            260                 265                 270
```

<210> SEQ ID NO 18
<211> LENGTH: 257
<212> TYPE: PRT
<213> ORGANISM: Phyllostachys praecox

<400> SEQUENCE: 18

```
Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser Gln Ala Ser Asn Met
50                  55                  60

Glu Gly Ile Leu Asp Arg Tyr Gln Arg Tyr Ser Phe Glu Glu Arg Ala
65                  70                  75                  80

Val Leu Asp Pro Asn Ile Gly Asp Gln Ala Asn Trp Gly Asp Glu Cys
                85                  90                  95
```

```
Gly Arg Leu Lys Thr Lys Leu Glu Ala Ile Gln Lys Ser Gln Arg Gln
                100                 105                 110

Leu Leu Gly Glu Gln Leu Asp Ala Leu Thr Ile Lys Glu Leu Gln Gln
        115                 120                 125

Leu Glu Gln Gln Leu Asp Ser Ser Leu Lys His Ile Arg Ser Arg Lys
    130                 135                 140

Asn Gln Leu Leu Phe Asp Ser Ile Ser Glu Leu Gln Lys Lys Glu Lys
145                 150                 155                 160

Ser Leu Thr Asp Gln Asn Gly Gln Leu Gln Lys His Leu Val Glu Thr
                165                 170                 175

Glu Lys Gly Lys Glu Lys Ser Asn Ala Leu Leu Ser Thr His His Arg
            180                 185                 190

Glu Gln Pro Asn Gly Ala Thr Thr Ser Ser Pro Ser Pro Ala Ala Val
        195                 200                 205

Thr Val Pro Tyr Ser Met Pro Thr Leu Asn Ile Gly Ser Tyr Gln Ser
    210                 215                 220

Lys Gly Ala Gly Gly Glu Ala Glu Pro Gln Pro Ser Pro Ala Gln Val
225                 230                 235                 240

Asn Ser Gly Lys Leu Pro Pro Trp Met Leu Gly Ser Val Asn Ile Asn
                245                 250                 255

Thr

<210> SEQ ID NO 19
<211> LENGTH: 201
<212> TYPE: PRT
<213> ORGANISM: Zea mays

<400> SEQUENCE: 19

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser His Ser Ser Met Glu
    50                  55                  60

Gly Ile Leu Glu Arg Tyr Gln Arg Tyr Ser Phe Glu Glu Arg Ala Val
65                  70                  75                  80

Leu Asn Pro Ser Ile Glu Asp Gln Ala Asn Trp Gly Asp Glu Tyr Val
                85                  90                  95

Arg Leu Lys Ser Lys Leu Asp Ala Leu Gln Lys Ser Gln Arg Gln Leu
                100                 105                 110

Leu Gly Glu Gln Leu Ser Ser Leu Thr Ile Lys Glu Leu Gln Gln Leu
        115                 120                 125

Glu Gln Gln Leu Asp Ser Ser Leu Lys His Ile Arg Ser Arg Lys Asn
    130                 135                 140

Gln Leu Met Phe Asp Ser Ile Ser Ala Leu Gln Lys Lys Val Ser Tyr
145                 150                 155                 160

Thr Leu Asp Ser Leu Val Pro Gly Ile Leu Arg Val Leu His Glu Ser
                165                 170                 175

Leu Val Lys Ile Ile Val Thr Ser Thr Pro Pro Ala Phe Gly Glu Leu
            180                 185                 190

Glu Gln Thr Leu Thr Ser Val Thr Ser
        195                 200
```

<210> SEQ ID NO 20
<211> LENGTH: 265
<212> TYPE: PRT
<213> ORGANISM: Hordeum vulgare subsp. vulgare

<400> SEQUENCE: 20

Met Gly Arg Gly Pro Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser Gln Asp Ser Ser Met
50                  55                  60

Asp Val Ile Leu Glu Arg Tyr Gln Arg Tyr Ser Phe Glu Glu Arg Ala
65                  70                  75                  80

Val Leu Asp Pro Ser Thr Gly Asp Gln Ala Asn Trp Gly Asp Glu Tyr
                85                  90                  95

Gly Ser Leu Lys Ile Lys Leu Asp Ala Leu Gln Lys Ser Gln Arg Gln
            100                 105                 110

Leu Leu Gly Glu Gln Leu Asp Pro Leu Thr Thr Lys Glu Leu Gln Gln
        115                 120                 125

Leu Glu Gln Gln Leu Asp Ser Ser Leu Lys His Ile Arg Ser Arg Lys
130                 135                 140

Asn Gln Leu Leu Phe Glu Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Asn Asn Val Leu Ser Asn Ile His His Arg Glu Gln
            180                 185                 190

Leu Asn Glu Ala Thr Asn Ile His His Gln Glu Gln Leu Ser Gly Ala
        195                 200                 205

Thr Thr Ser Ser Pro Ser Pro Thr Pro Thr Ala Gln Asp Ser Met
210                 215                 220

Ala Pro Pro Asn Ile Gly Pro Tyr Gln Ser Arg Gly Gly Gly Asp Pro
225                 230                 235                 240

Glu Pro Gln Pro Ser Pro Ala Gln Ala Asn Asn Ser Asn Leu Pro Pro
                245                 250                 255

Trp Met Leu Arg Thr Ile Gly Asn Arg
            260                 265

<210> SEQ ID NO 21
<211> LENGTH: 267
<212> TYPE: PRT
<213> ORGANISM: Aegilops tauschii subsp. tauschii

<400> SEQUENCE: 21

Met Gly Arg Gly Pro Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser Gln Asp Ser Ser Met
50                  55                  60

Asp Val Ile Leu Glu Arg Tyr Gln Arg Tyr Ser Phe Glu Glu Arg Ala
65                  70                  75                  80

Val Leu Asp Pro Ser Ile Gly Asn Gln Ala Asn Trp Gly Asp Glu Tyr
                85                  90                  95

Gly Ser Leu Lys Ile Lys Leu Asp Ala Leu Gln Lys Ser Gln Arg Gln
            100                 105                 110

Leu Leu Gly Glu Gln Leu Asp Pro Leu Thr Thr Lys Glu Leu Gln Gln
        115                 120                 125

Leu Glu Gln Gln Leu Asp Ser Ser Leu Lys His Ile Arg Ser Arg Lys
    130                 135                 140

Asn Gln Leu Leu Phe Glu Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Asn Asn Val Leu Ser Asn Ile His His Gln Glu Gln
            180                 185                 190

Leu Asn Gly Ala Thr Asn Ile His His Gln Glu Gln Leu Asn Gly Ala
        195                 200                 205

Thr Thr Ser Ser Pro Ser Pro Thr Pro Ala Thr Ala Gln Asp Ser Met
    210                 215                 220

Ala Thr Pro Asn Ile Gly Pro Tyr Gln Ser Arg Glu Ser Gly Gly Gly
225                 230                 235                 240

Asn Pro Glu Pro Gln Pro Ser Pro Ala Gln Ala Asn Asn Ser Asn Leu
                245                 250                 255

Pro Pro Trp Met Leu Ser Thr Ile Ser Asn Arg
            260                 265

<210> SEQ ID NO 22
<211> LENGTH: 267
<212> TYPE: PRT
<213> ORGANISM: Triticum aestivum

<400> SEQUENCE: 22

Met Gly Arg Gly Pro Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Ala Leu Ile Val Phe
            35                  40                  45

Ser Thr Lys Gly Lys Leu Tyr Glu Tyr Ser Ser Gln Asp Ser Ser Met
        50                  55                  60

Asp Val Ile Leu Glu Arg Tyr Gln Arg Tyr Ser Phe Glu Glu Arg Ala
65                  70                  75                  80

Val Leu Asp Pro Ser Ile Gly Asn Gln Ala Asn Trp Gly Asp Glu Tyr
                85                  90                  95

Gly Ser Leu Lys Ile Lys Leu Asp Ala Leu Gln Lys Ser Gln Arg Gln
            100                 105                 110

Leu Leu Gly Glu Gln Leu Asp Pro Leu Thr Thr Lys Glu Leu Gln Gln
        115                 120                 125

Leu Glu Gln Gln Leu Asp Ser Ser Leu Lys His Ile Arg Ser Arg Lys
    130                 135                 140

Asn Gln Leu Leu Phe Glu Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Asn Asn Val Leu Ser Asn Ile His His Gln Glu Gln
            180                 185                 190

Leu Asn Gly Ala Thr Asn Ile Asn His Gln Glu Gln Leu Asn Gly Ala
            195                 200                 205

Thr Thr Ser Ser Pro Ser Pro Thr Pro Ala Thr Ala Gln Asp Ser Met
    210                 215                 220

Ala Thr Pro Asn Ile Gly Pro Tyr Gln Ser Arg Glu Ser Gly Gly Gly
225                 230                 235                 240

Asn Pro Glu Pro Gln Pro Ser Pro Ala Gln Ala Asn Asn Ser Asn Leu
            245                 250                 255

Pro Pro Trp Met Leu Ser Thr Ile Ser Asn Arg
            260                 265

<210> SEQ ID NO 23
<211> LENGTH: 253
<212> TYPE: PRT
<213> ORGANISM: Brachypodium distachyon

<400> SEQUENCE: 23

Met Gly Arg Gly Pro Val Gln Leu Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser Gln Asp Ser Ser Met
    50                  55                  60

Asp Val Ile Leu Glu Arg Tyr Gln Arg Tyr Ser Phe Glu Glu Arg Ala
65                  70                  75                  80

Val Leu Asp Pro Asn Ile Gly Asp Gln Ala Asn Trp Gly Asp Glu Tyr
                85                  90                  95

Gly Arg Leu Lys Ile Lys Leu Asp Ala Leu Gln Lys Ser Gln Arg Gln
            100                 105                 110

Leu Leu Gly Glu Gln Leu Glu Pro Leu Thr Thr Arg Glu Leu Gln Gln
        115                 120                 125

Leu Glu Gln Gln Leu Asp Ser Ser Leu Lys His Ile Arg Ser Arg Lys
    130                 135                 140

Asn Gln Leu Leu Phe Asp Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Asn Asn Ala Leu Ser Asn Ile Gln His Arg Glu Gln
            180                 185                 190

Leu Asn Glu Lys Asn Thr Ala Leu Pro Asn Thr His Asp Arg Glu Gln
        195                 200                 205

Gln Asn Gly Ala Thr Thr Ser Ser Pro Ser Pro Thr Pro Leu Thr Val
    210                 215                 220

Leu Asp Ser Met Pro Asn Leu Asn Ile Gly Tyr Tyr Ala Ser His Ile
225                 230                 235                 240

His Cys Ile Asp Val Cys Ser Arg Met Tyr Arg Gln Ile
                245                 250

<210> SEQ ID NO 24
<211> LENGTH: 267
<212> TYPE: PRT

<213> ORGANISM: Triticum aestivum

<400> SEQUENCE: 24

Met Gly Arg Gly Pro Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser Gln Asp Ser Ser Met
50                  55                  60

Asp Val Ile Leu Glu Arg Tyr Gln Arg Tyr Ser Phe Glu Glu Arg Ala
65                  70                  75                  80

Val Leu Asp Pro Ser Ile Gly Asn Gln Ala Asn Trp Gly Asp Glu Tyr
                85                  90                  95

Gly Ser Leu Lys Ile Lys Leu Asp Ala Phe Gln Lys Ser Gln Arg Gln
            100                 105                 110

Leu Leu Gly Glu Gln Leu Gly Pro Leu Thr Thr Lys Glu Leu Gln Gln
        115                 120                 125

Leu Glu Gln Gln Leu Asp Ser Ser Leu Lys His Ile Arg Ser Arg Lys
130                 135                 140

Asn Gln Leu Leu Phe Glu Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Asn Asn Val Leu Ser Asn Ile His His Gln Glu Gln
            180                 185                 190

Leu Asn Gly Ala Thr Asn Ile Asn His Gln Glu Gln Leu Asn Gly Ala
        195                 200                 205

Thr Thr Ser Ser Pro Ser Pro Thr Pro Ala Thr Ala Gln Asp Ser Met
210                 215                 220

Ala Thr Pro Asn Ile Gly Pro Tyr Gln Ser Ser Glu Ser Gly Gly Gly
225                 230                 235                 240

Asn Pro Glu Pro Gln Pro Ser Pro Ala Gln Ala Asn Asn Ser Asn Leu
                245                 250                 255

Pro Pro Trp Met Leu Ser Thr Ile Ser Ser Arg
            260                 265

<210> SEQ ID NO 25
<211> LENGTH: 279
<212> TYPE: PRT
<213> ORGANISM: Lolium perenne

<400> SEQUENCE: 25

Met Gly Arg Gly Pro Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser Gln Asp Ser Asn Met
50                  55                  60

Asp Val Ile Leu Glu Arg Tyr Gln Arg Tyr Ser Phe Glu Glu Arg Ala
65                  70                  75                  80

Ile Val Asp Gln Asn Ile Gly Gly Gln Ala Asn Trp Gly Asp Glu Phe

```
                        85                  90                  95
Gly Ser Leu Lys Ile Lys Leu Asp Ala Leu Gln Lys Ser Gln Arg Gln
            100                 105                 110

Leu Leu Gly Glu Gln Leu Asp Pro Leu Thr Thr Lys Glu Leu Gln Gln
            115                 120                 125

Leu Glu Gln Gln Leu Asp Ser Ser Leu Lys His Ile Arg Ser Arg Lys
            130                 135                 140

Asn Gln Leu Leu Phe Glu Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Ser Asn Val Leu Ser Asn Ile His His Arg Glu Gln
            180                 185                 190

Thr Asn Gly Ala Ala Asn Ile His Arg Arg Glu Gln Met Asn Glu Thr
            195                 200                 205

Thr His Ile His Asn Gln Glu Gln Leu Asn Gly Ala Thr Thr Ser Ser
            210                 215                 220

Pro Ser Pro Thr Pro Val Ala Val Leu Asp Ser Val Ala Thr Leu Asn
225                 230                 235                 240

Ile Gly Ser Ser Gln Ser Arg Glu Ala Ala Gly Glu Glu Pro Glu Ser
                245                 250                 255

Gln Pro Ser Pro Ala Gln Ala Asn Ser Gly Lys Leu Pro Pro Trp Met
                260                 265                 270

Leu Arg Thr Ile Ser Asn Arg
            275

<210> SEQ ID NO 26
<211> LENGTH: 249
<212> TYPE: PRT
<213> ORGANISM: Oryza sativa Indica Group

<400> SEQUENCE: 26

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Asp Val Ala Leu Ile Val Phe
        35                  40                  45

Ser Thr Lys Gly Lys Leu Tyr Glu Phe Ser Ser His Ser Met Glu
    50                  55                  60

Gly Ile Leu Glu Arg Tyr Gln Arg Tyr Ser Phe Asp Glu Arg Ala Val
65                  70                  75                  80

Leu Glu Pro Asn Thr Glu Asp Gln Glu Asn Trp Gly Asp Glu Tyr Gly
                85                  90                  95

Ile Leu Lys Ser Lys Leu Asp Ala Leu Gln Lys Ser Gln Arg Gln Leu
            100                 105                 110

Leu Gly Glu Gln Leu Asp Thr Leu Thr Thr Lys Glu Leu Gln Gln Leu
            115                 120                 125

Glu His Gln Leu Glu Tyr Ser Leu Lys His Ile Arg Ser Lys Lys Asn
            130                 135                 140

Gln Leu Leu Phe Glu Ser Ile Ser Glu Leu Gln Lys Lys Glu Lys Ser
145                 150                 155                 160

Leu Lys Asn Gln Asn Asn Val Leu Gln Lys Leu Met Glu Thr Glu Lys
                165                 170                 175
```

```
Glu Lys Asn Asn Ala Ile Ile Asn Thr Asn Arg Glu Glu Gln Asn Gly
                180                 185                 190

Ala Thr Pro Ser Thr Ser Ser Pro Thr Pro Val Thr Ala Pro Asp Pro
            195                 200                 205

Ile Pro Thr Thr Asn Asn Ser Gln Ser Gln Pro Arg Gly Ser Gly Glu
    210                 215                 220

Ser Glu Ala Gln Pro Ser Pro Ala Gln Ala Gly Asn Ser Lys Leu Pro
225                 230                 235                 240

Pro Trp Met Leu Arg Thr Ser His Thr
                245
```

<210> SEQ ID NO 27
<211> LENGTH: 309
<212> TYPE: PRT
<213> ORGANISM: Brachypodium distachyon

<400> SEQUENCE: 27

```
Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
                20                  25                  30

His Glu Ile Ser Val Leu Cys Asp Ala Glu Val Ala Leu Ile Val Phe
            35                  40                  45

Ser Thr Lys Gly Lys Leu Tyr Glu Tyr Ser Ser Gln Asp Ser Ser Met
    50                  55                  60

Asp Val Ile Leu Glu Arg Tyr Gln Arg Tyr Ser Phe Glu Glu Arg Ala
65                  70                  75                  80

Val Leu Asp Pro Asn Ile Gly Asp Gln Ala Asn Trp Gly Asp Glu Tyr
                85                  90                  95

Gly Arg Leu Lys Ile Lys Leu Asp Ala Leu Gln Lys Ser Gln Arg Gln
            100                 105                 110

Leu Leu Gly Glu Gln Leu Glu Pro Leu Thr Thr Arg Glu Leu Gln Gln
    115                 120                 125

Leu Glu Gln Gln Leu Asp Ser Ser Leu Lys His Ile Arg Ser Arg Lys
130                 135                 140

Asn Gln Leu Leu Phe Asp Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Asn Asn Ala Leu Ser Asn Ile Gln His Arg Glu Gln
            180                 185                 190

Leu Asn Glu Lys Asn Thr Ala Leu Pro Asn Thr His Asp Arg Glu Gln
    195                 200                 205

Gln Asn Gly Ala Thr Thr Ser Ser Pro Ser Pro Thr Pro Leu Thr Val
210                 215                 220

Leu Asp Ser Met Pro Asn Leu Asn Ile Gly Tyr Tyr Ala Ser His Ile
225                 230                 235                 240

His Cys Ile Asp Val Cys Ser Arg His Ile Asn Leu Glu Lys Gln Glu
                245                 250                 255

Glu Asn Gln Asn Leu Ser Arg Leu Gln His Lys Gln Thr Ala Ala Ser
            260                 265                 270

Tyr Arg His Gly Cys Ser Ala Pro Ser Val Thr Asp Glu Gly Phe Gln
    275                 280                 285

Cys Pro His Val Thr Leu His Pro Lys Gly Ile Ser Val Pro Ser Gly
290                 295                 300
```

Val His His Gly Ser
305

<210> SEQ ID NO 28
<211> LENGTH: 250
<212> TYPE: PRT
<213> ORGANISM: Oryza brachyantha

<400> SEQUENCE: 28

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Arg Glu Ile Ser Val Leu Cys Asp Ala Asp Val Ala Leu Ile Val Phe
        35                  40                  45

Ser Thr Lys Gly Lys Leu Tyr Glu Phe Ser Ser His Ser Ser Met Glu
    50                  55                  60

Gly Ile Leu Glu Arg Tyr Gln Arg Tyr Ser Phe Asp Glu Lys Ala Ala
65                  70                  75                  80

Leu Asp Pro Asn Thr Glu Asp Gln Glu Asn Trp Gly Asp Glu Tyr Gly
                85                  90                  95

Ile Leu Lys Ser Lys Leu Asp Ala Leu Gln Lys Ser Gln Arg Gln Leu
            100                 105                 110

Leu Gly Glu Gln Leu Asp Thr Leu Thr Thr Lys Glu Leu Gln Gln Leu
        115                 120                 125

Glu His Gln Leu Glu His Ser Leu Lys His Ile Arg Ser Lys Lys Asn
    130                 135                 140

Gln Leu Leu Phe Glu Ser Ile Ser Glu Leu Gln Lys Lys Glu Lys Ser
145                 150                 155                 160

Leu Lys Asn Gln Asn Ser Val Leu Gln Lys Leu Met Glu Thr Glu Lys
                165                 170                 175

Lys Lys Ile Asn Val Ala Ala Asn Thr His Arg Glu Glu Gln Asn Ile
            180                 185                 190

Thr Thr Ala Ser Thr Ser Ser Pro Thr Pro Val Ala Ala Pro Glu Ser
        195                 200                 205

Thr Pro Thr Ile Asn Ala Gly Gln Asn Gln Pro Arg Gly Ser Gly Glu
    210                 215                 220

Ser Glu Ala Gln Pro Ser Pro Ala Gln Ala Ser Ser Lys Leu Pro
225                 230                 235                 240

Pro Trp Met Leu Arg Thr Val Ser Asn Thr
                245                 250

<210> SEQ ID NO 29
<211> LENGTH: 289
<212> TYPE: PRT
<213> ORGANISM: Hordeum vulgare subsp. vulgare

<400> SEQUENCE: 29

Met Gly Arg Gly Pro Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser Gln Asp Ser Ser Met
    50                  55                  60

```
Asp Val Ile Leu Glu Arg Tyr Gln Arg Tyr Ser Phe Glu Glu Arg Ala
 65                  70                  75                  80

Val Leu Asp Pro Ser Thr Gly Asp Gln Ala Asn Trp Gly Asp Glu Tyr
                 85                  90                  95

Gly Ser Leu Lys Ile Lys Leu Asp Ala Leu Gln Lys Ser Gln Arg Gln
            100                 105                 110

Leu Leu Gly Glu Gln Leu Asp Pro Leu Thr Thr Lys Glu Leu Gln Gln
        115                 120                 125

Leu Glu Gln Gln Leu Asp Ser Ser Leu Lys His Ile Arg Ser Arg Lys
130                 135                 140

Asn Gln Leu Leu Phe Glu Ser Ile Ser Glu Leu Gln Lys Lys Glu Lys
145                 150                 155                 160

Ser Leu Lys Asp Gln Asn Gly Val Leu Gln Lys His Leu Val Glu Thr
                165                 170                 175

Glu Lys Glu Lys Asn Asn Val Leu Ser Asn Ile His His Arg Glu Gln
            180                 185                 190

Leu Asn Glu Ala Thr Asn Ile His His Gln Glu Gln Leu Ser Gly Ala
        195                 200                 205

Thr Thr Ser Ser Pro Ser Pro Thr Pro Pro Thr Ala Gln Asp Ser Met
210                 215                 220

Ala Pro Pro Asn Ile Gly Tyr Leu Cys Phe His Leu Gly His Ile Asn
225                 230                 235                 240

Leu Glu Glu Glu Gly Ile Gln Asn Leu Ser Arg His Gln His Lys Gln
                245                 250                 255

Thr Thr Ala Ile Cys His Arg Gly Cys Ser Ala Pro Ser Ala Thr Asp
            260                 265                 270

Glu Gly Trp Arg Gln Pro His Thr Thr Pro Pro Glu Gly Asp Asn Gly
        275                 280                 285

Ala

<210> SEQ ID NO 30
<211> LENGTH: 291
<212> TYPE: PRT
<213> ORGANISM: Aegilops tauschii subsp. tauschii

<400> SEQUENCE: 30

Met Gly Arg Gly Pro Val Gln Leu Arg Arg Ile Glu Asn Lys Ile Asn
  1               5                  10                  15

Arg Gln Val Thr Phe Ser Lys Arg Arg Ser Gly Leu Leu Lys Lys Ala
             20                  25                  30

His Glu Ile Ser Val Leu Cys Asp Ala Glu Val Ala Leu Ile Val Phe
         35                  40                  45

Ser Thr Lys Gly Lys Leu Tyr Glu Tyr Ser Ser Gln Asp Ser Ser Met
     50                  55                  60

Asp Val Ile Leu Glu Arg Tyr Gln Arg Tyr Ser Phe Glu Glu Arg Ala
 65                  70                  75                  80

Val Leu Asp Pro Ser Ile Gly Asn Gln Ala Asn Trp Gly Asp Glu Tyr
                 85                  90                  95

Gly Ser Leu Lys Ile Lys Leu Asp Ala Leu Gln Lys Ser Gln Arg Gln
            100                 105                 110

Leu Leu Gly Glu Gln Leu Asp Pro Leu Thr Thr Lys Glu Leu Gln Gln
        115                 120                 125

Leu Glu Gln Gln Leu Asp Ser Ser Leu Lys His Ile Arg Ser Arg Lys
130                 135                 140
```

```
Asn Gln Leu Leu Phe Glu Ser Ile Ser Glu Leu Gln Lys Lys Glu Lys
145                 150                 155                 160

Ser Leu Lys Asp Gln Asn Gly Val Leu Gln Lys His Leu Val Glu Thr
            165                 170                 175

Glu Lys Glu Lys Asn Asn Val Leu Ser Asn Ile His His Gln Glu Gln
        180                 185                 190

Leu Asn Gly Ala Thr Asn Ile His His Gln Glu Gln Leu Asn Gly Ala
    195                 200                 205

Thr Thr Ser Ser Pro Ser Pro Thr Pro Ala Thr Ala Gln Asp Ser Met
210                 215                 220

Ala Thr Pro Asn Ile Gly Tyr Leu Cys Phe His Leu Gly His Ile Asn
225                 230                 235                 240

Leu Glu Asn Gln Glu Gly Gly Ile Gln Asn Leu Ser Arg Leu Gln His
                245                 250                 255

Lys Gln Thr Thr Ala Ile Tyr His Arg Gly Cys Ser Pro Pro Ser Ala
            260                 265                 270

Thr Asp Glu Gly Trp Arg Gln Pro His Met Thr Pro Pro Glu Gly Glu
        275                 280                 285

Asn Gly Ala
    290

<210> SEQ ID NO 31
<211> LENGTH: 250
<212> TYPE: PRT
<213> ORGANISM: Phoenix dactylifera

<400> SEQUENCE: 31

Met Gly Arg Gly Arg Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Ile Phe
        35                  40                  45

Ser Thr Lys Gly Lys Leu Tyr Glu Tyr Ala Thr Asp Ser Cys Met Glu
50                  55                  60

Arg Ile Leu Glu Arg Tyr Glu Arg Tyr Thr Tyr Ala Glu Lys Ala Leu
65                  70                  75                  80

Val Ser Ser Gly Pro Glu Ser Gln Gly Asp Trp Cys His Glu Tyr Gly
                85                  90                  95

Lys Leu Lys Ala Met Val Glu Ala Leu Gln Lys Ser Gln Arg His Leu
            100                 105                 110

Met Gly Glu Gln Leu Glu Ser Leu Asn Leu Lys Glu Leu Gln Gln Leu
        115                 120                 125

Glu Gln Gln Leu Glu Asn Ser Leu Lys His Ile Arg Ser Arg Lys Cys
    130                 135                 140

Gln Leu Met Phe Asp Ser Ile Ser Glu Leu Gln Lys Lys Glu Lys Ser
145                 150                 155                 160

Leu Gln Glu Gln Asn Lys Met Leu Glu Lys Glu Leu Met Glu Lys Gln
                165                 170                 175

Lys Val Lys Ala Leu Asn Gln Gln Ala His Trp Glu Gln Gln Gly Leu
            180                 185                 190

Pro Gln Thr Cys Pro Ser Ser Pro Ser Phe Leu Ile Gly Asp Ser
    195                 200                 205

Leu Pro Thr Leu Asn Ile Gly Thr Tyr Gln Cys Ser Gly Asn Glu His
```

```
                210                 215                 220
Gly Glu Glu Ala Ala Gln Arg Gln Val Arg Ile Gly Asn Ser Leu Leu
225                 230                 235                 240

Pro Pro Trp Met Leu Ser His Leu Asn Gly
                245                 250

<210> SEQ ID NO 32
<211> LENGTH: 250
<212> TYPE: PRT
<213> ORGANISM: Elaeis guineensis

<400> SEQUENCE: 32

Met Gly Arg Gly Arg Val Gln Leu Arg Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Ala Leu Ile Ile Phe
            35                  40                  45

Ser Thr Lys Gly Lys Leu Tyr Glu Tyr Ala Thr Asp Ser Cys Met Glu
        50                  55                  60

Arg Ile Leu Glu Arg Tyr Glu Arg Tyr Thr Tyr Ala Glu Lys Ala Leu
65                  70                  75                  80

Ile Ser Ser Gly Pro Glu Leu Gln Gly Asn Trp Cys His Glu Phe Gly
                85                  90                  95

Lys Leu Lys Ala Lys Val Glu Ala Leu Gln Lys Ser Gln Arg His Leu
                100                 105                 110

Met Gly Glu Gln Leu Glu Pro Leu Asn Leu Lys Glu Leu Gln Gln Leu
            115                 120                 125

Glu Gln Gln Leu Glu Ser Ser Leu Lys His Ile Arg Thr Arg Lys Cys
        130                 135                 140

Gln Leu Met Phe Glu Ser Ile Ser Glu Leu Gln Lys Lys Glu Lys Ser
145                 150                 155                 160

Leu Gln Glu Gln Asn Lys Met Leu Gly Lys Glu Leu Met Glu Lys Gln
                165                 170                 175

Lys Val Lys Ala Leu Asn Gln Gln Ala Pro Trp Glu Gln Gln Gly Pro
                180                 185                 190

Pro Gln Thr Ser Ser Ser Ser Pro Thr Ser Phe Leu Ile Gly Asp Ser
            195                 200                 205

Leu Pro Thr Leu Asn Ile Gly Thr Tyr Gln Cys Ser Gly Asn Glu His
        210                 215                 220

Gly Glu Glu Ala Ala Gln Pro Gln Val Arg Ile Gly Asn Ser Leu Leu
225                 230                 235                 240

Pro Pro Trp Met Leu Ser His Leu Asn Gly
                245                 250

<210> SEQ ID NO 33
<211> LENGTH: 248
<212> TYPE: PRT
<213> ORGANISM: Ananas comosus

<400> SEQUENCE: 33

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Ala Leu Ile Ile Phe
```

-continued

```
                35                  40                  45
Ser Thr Lys Gly Lys Leu Tyr Glu Tyr Ala Thr Asp Ser Ser Met Glu
 50                      55                  60

Lys Ile Leu Glu Arg Tyr Glu Arg Tyr Ser Tyr Ala Glu Lys Ala Leu
 65                  70                  75                  80

Val Ser Ala Asp Pro Glu Ser Gln Gly Asn Trp Cys His Glu Tyr Ser
                 85                  90                  95

Lys Leu Lys Ala Arg Val Glu Ala Ile Gln Lys Ser Gln Arg His Leu
            100                 105                 110

Met Gly Glu Gln Leu Glu Ser Leu Asn Leu Lys Glu Leu Gln Gln Leu
        115                 120                 125

Glu Gln Gln Leu Glu Ser Ser Leu Lys His Ile Arg Ser Arg Lys Ser
    130                 135                 140

Gln Leu Leu Leu Asp Ser Ile Ser Glu Leu Lys Arg Lys Glu Lys Ser
145                 150                 155                 160

Leu Gln Glu His Asn Lys Ala Leu Glu Lys Glu Leu Met Glu Lys Gln
                165                 170                 175

Lys Ala Leu Thr Gln Gln His Trp Glu Gln Gln Thr Gln Pro Pro
            180                 185                 190

Thr Asn Ser Ser Ser Pro Leu Ser Phe Leu Leu Pro Thr Asp Ser Leu
        195                 200                 205

Pro Thr Leu Asn Ile Gly Thr Tyr Gln Ala Thr Gly Thr Gly Ala Glu
    210                 215                 220

Glu Val Glu Gly Ile Ala Gln Pro Gln Ala Arg Met Gly Leu Pro Pro
225                 230                 235                 240

Trp Met Val Arg His Leu Asn Gly
                245

<210> SEQ ID NO 34
<211> LENGTH: 252
<212> TYPE: PRT
<213> ORGANISM: Alstroemeria ligtu subsp. ligtu

<400> SEQUENCE: 34

Met Gly Arg Gly Arg Val Gln Leu Lys Arg Ile Glu Asn Lys Ile Asn
 1               5                  10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Thr Asp Ala Ser Met Glu
 50                  55                  60

Met Ile Leu Glu Arg Tyr Glu Arg Tyr Ser Gln Ala Glu Arg Ala Val
 65                  70                  75                  80

Ser Glu Ala Asp Pro Glu Ser Gln Gly Asn Trp Ile His Glu His Ser
                 85                  90                  95

Lys Leu Lys Ser Lys Asp Glu Ala Leu Gln Lys Asn Gln Arg His Leu
            100                 105                 110

Met Gly Glu Gln Leu Asp Asn Leu Ser His Lys Glu Leu Gln His Leu
        115                 120                 125

Glu Gln Gln Leu Glu Gly Ala Leu Lys His Ile Arg Ser Lys Lys Asn
    130                 135                 140

Gln Leu Leu Ser Asp Ser Val Ser Glu Leu Gln Arg Lys Glu Lys Phe
145                 150                 155                 160
```

```
Leu Gln Glu Gln Asn Arg Leu Leu Glu Asn Lys Leu Ile Glu Lys Glu
                165                 170                 175

Lys Glu Lys Ala Lys Ala Leu Met Gln His Ala His Trp Glu Gln Gln
            180                 185                 190

Gly Gln Ala Gln Thr Ser Ser Ser Pro Thr Phe Leu Met Thr Glu
        195                 200                 205

Gln Leu Pro Ser Leu Asn Met Gly Thr Tyr Gln Gly Gly Ala Gly Asn
    210                 215                 220

Ala Glu Glu Gly Val Ala Gly Gln Thr Leu Pro Arg Ala Gly Ser Asn
225                 230                 235                 240

Thr Leu Pro Pro Trp Met Leu Arg His Val Ser Gly
                245                 250

<210> SEQ ID NO 35
<211> LENGTH: 246
<212> TYPE: PRT
<213> ORGANISM: Musa acuminata subsp. malaccensis

<400> SEQUENCE: 35

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Thr Asp Ser Ser Met Glu
    50                  55                  60

Lys Ile Leu Glu Arg Tyr Glu Tyr Tyr Ser Tyr Ala Glu Lys Ala Leu
65                  70                  75                  80

Met Ser Ser Asp Gln Asp Tyr Gln Gly Asn Trp Cys Gln Glu Tyr Gly
                85                  90                  95

Lys Leu Lys Ala Lys Val Glu Ala Leu Ser Lys Ser Gln Arg His Leu
            100                 105                 110

Met Gly Glu Gln Leu Glu Ala Leu Asn Leu Lys Glu Leu Gln Gln Leu
        115                 120                 125

Glu His Gln Leu Glu Ile Ser Leu Lys His Ile Arg Ser Arg Lys Asn
    130                 135                 140

Gln Val Met Phe Asp Ser Ile Ala Glu Leu Gln Lys Lys Glu Lys Ala
145                 150                 155                 160

Leu Gln Ala Ala Asn Lys Thr Leu Glu Gln Glu Leu Met Glu Lys Gln
                165                 170                 175

Lys Ile Lys Ala Ile Thr Gln Gln Ala His Trp Glu Gln Ala Gln Thr
            180                 185                 190

Ser Ser Ser Ser Pro Pro Leu Ile Ala Glu Pro Gln Pro Thr Leu
        195                 200                 205

Asn Ile Gly Cys Tyr Gln Gly Met Ala Leu Ala Val Arg Glu Glu Ala
    210                 215                 220

Ser Arg Leu Pro Val Arg Ile Ser Asn Ser Leu Leu Pro Pro Trp Met
225                 230                 235                 240

Leu Arg His Leu Asn Gly
                245

<210> SEQ ID NO 36
<211> LENGTH: 240
<212> TYPE: PRT
<213> ORGANISM: Tricyrtis sp. Shinonome
```

<400> SEQUENCE: 36

```
Met Gly Arg Gly Arg Val Gln Leu Lys Arg Ile Glu Asn Lys Ile Ser
1               5                   10                  15

Arg Gln Val Thr Phe Ser Lys Arg Arg Pro Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Thr Asp Ser Ser Met Glu
    50                  55                  60

Lys Ile Leu Glu Arg Tyr Glu Ser Tyr Ser Leu Ser Glu Arg Ala Val
65                  70                  75                  80

Met Asp Ala Asp Pro Glu Ser Gln Ala Ser Trp Trp His Glu Tyr Arg
                85                  90                  95

Arg Leu Lys Ala Arg Val Asp Thr Ile Gln Lys Thr Gln Arg His Leu
            100                 105                 110

Met Gly Glu Gln Leu Asp Asn Leu Ser Leu Lys Glu Leu Gln Gln Leu
        115                 120                 125

Glu Gln Gln Leu Glu Asn Ala Ile Lys His Ile Arg Ser Arg Lys Asn
130                 135                 140

Gln Leu Leu Phe Glu Ser Ile Ser Glu Leu Gln Gln Lys Glu Lys Ser
145                 150                 155                 160

Leu Gln Glu Gln Asn Asn Ile Leu Glu Lys Lys Leu Gln Asp Lys Arg
                165                 170                 175

Lys Ala Glu Ala Leu Thr Gln Asn Glu Arg Ser Phe Leu Met Ser Asp
            180                 185                 190

Pro Leu Pro Thr Thr Leu Asn Ile Gly Ala Tyr Gln Val Thr Arg Gly
        195                 200                 205

Arg Gly Ser Val Glu Glu Asp Ala Gly Glu Gly Cys Pro Leu Ala Gln
    210                 215                 220

Ser Gly Ser Thr Thr Leu Pro Pro Trp Met Leu Arg His Val Asp Gly
225                 230                 235                 240
```

<210> SEQ ID NO 37
<211> LENGTH: 245
<212> TYPE: PRT
<213> ORGANISM: Musa acuminata subsp. malaccensis

<400> SEQUENCE: 37

```
Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Thr Asp Ser Ser Met Glu
    50                  55                  60

Arg Ile Leu Glu Arg Tyr Gln Gln Tyr Ser Tyr Ala Glu Arg Ala Leu
65                  70                  75                  80

Leu Glu Ala Asp Thr Glu Val Gln Gly Asn Trp Cys Leu Glu Tyr Gly
                85                  90                  95

Gln Leu Lys Ala Lys Ile Glu Ala Leu Gln Thr Ser Gln Arg His Leu
            100                 105                 110

Val Gly Glu Gln Leu Glu Lys Leu Thr Leu Lys Glu Leu Gln Gln Leu
        115                 120                 125
```

Glu Gln Gln Leu Glu Thr Ala Leu Arg Lys Ile Arg Ser Arg Lys Asn
            130                 135                 140

Asn Val Leu Phe Asp Ser Ile His Glu Leu Gln Arg Lys Glu Lys Ala
145                 150                 155                 160

Leu Gln Ala His Asn Ser Asn Leu Glu Lys Lys Ile Lys Glu Lys Asn
                165                 170                 175

Lys Glu Ala Glu Glu Ala Leu Ser Gln Gln Gln Ala Glu His Gln
                180                 185                 190

Ala Pro Ala Glu Thr Ser Ser Pro Pro Asp Leu Leu Ser Thr Asp
            195                 200                 205

Ser Thr Ile Asn Val Gly Asn Tyr Gln Ala Thr Gly Ala Val Val Glu
            210                 215                 220

Glu Ala Glu Gln Pro Leu Ala Gln Thr Thr Ser Ser Val Leu Pro Pro
225                 230                 235                 240

Trp Met Leu Arg Leu
                245

<210> SEQ ID NO 38
<211> LENGTH: 247
<212> TYPE: PRT
<213> ORGANISM: Alpinia oblongifolia

<400> SEQUENCE: 38

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Val Ile Ile Phe
            35                  40                  45

Ser Ser Lys Gly Lys Leu Tyr Glu Tyr Ser Thr Asp Ser Ser Met Glu
    50                  55                  60

Lys Ile Leu Glu Arg Tyr Glu Gln Tyr Cys Tyr Ala Glu Lys Ala Leu
65              70                  75                  80

Ile Ser Ser Glu Leu Asp Cys Gln Glu Asn Trp His His Glu Tyr Gly
                85                  90                  95

Lys Leu Lys Ala Lys Met Glu Ala Leu Ser Lys Ser Gln Arg His Leu
            100                 105                 110

Met Gly Glu Gln Leu Asp Thr Leu Ser Leu Lys Glu Leu Gln Gln Leu
            115                 120                 125

Glu Asn Gln Leu Asp Asn Ser Leu Lys His Ile Arg Ser Arg Lys Asn
            130                 135                 140

Gln Val Leu Leu Asp Ser Ile Ser Glu Leu Gln Val Lys Glu Lys Ala
145                 150                 155                 160

Leu Gln Glu Gln Asn Lys Ser Leu Glu Lys Gln Ile Leu Glu Lys Gln
                165                 170                 175

Lys Ala Lys Ala Leu Thr Gln Gln Ala His Trp Glu Gln Ala Gln Thr
            180                 185                 190

Ser Ser Ser Ser Pro Pro Phe Ile Leu Ala Asp Ala Asn Pro Thr Leu
            195                 200                 205

Asn Ile Gly Cys Tyr Gln Gly Arg Ala Thr Ile Glu Gly Glu Val Glu
            210                 215                 220

Ala Val Glu Gly Gln Ala Arg Ile Asn Asn Ser Met Leu Pro Pro Trp
225                 230                 235                 240

Met Leu Ser His Leu Asn Gly

<210> SEQ ID NO 39
<211> LENGTH: 250
<212> TYPE: PRT
<213> ORGANISM: Crocus sativus

<400> SEQUENCE: 39

Met Gly Arg Gly Arg Val Gln Leu Lys Arg Ile Glu Asn Thr Ile Asn
1               5                   10                  15

Arg Gln Val Thr Phe Ser Lys Arg Arg Ala Gly Leu Leu Lys Lys Ala
                20                  25                  30

Asn Glu Ile Ser Val Leu Cys Asp Ala Glu Val Ala Leu Ile Ile Phe
            35                  40                  45

Ser Thr Lys Gly Lys Leu Ser Glu Tyr Ser Thr Asp Ala Arg Met Glu
50                  55                  60

Ser Ile Leu Glu Arg Tyr Asp Arg Tyr Ser Ala Glu Arg Ala Ile
65                  70                  75                  80

Val Ala Pro Asp Pro Asp Ser Gln Glu Ser Trp Arg Asp Glu Tyr Gly
                85                  90                  95

Arg Leu Lys Ala Lys Leu Glu Ala Leu Gln Thr Ser Gln Arg His Leu
            100                 105                 110

Met Gly Ala Gln Leu Asp Met Leu Ser Val Lys Glu Leu Gln Gln Leu
        115                 120                 125

Glu Gln Gln Leu Glu Asn Ala Leu Lys Asn Ile Arg Thr Arg Lys Asn
130                 135                 140

Gln Leu Met Phe Asp Ser Ile Ser Glu Leu Gln Lys Lys Glu Lys Thr
145                 150                 155                 160

Leu Val Ser Gln Asn Lys Asp Leu Glu Lys Lys Leu Ile Glu Lys Glu
                165                 170                 175

Lys Gly Lys Ala Met Ala Gln Gln Gly His Trp Asp Gln Gln Gly Gln
            180                 185                 190

Gln Tyr Thr Glu Ser Ser Ser Pro Ser Leu Leu Ile Gln Asp Pro
        195                 200                 205

Phe Pro Ser Leu Thr Ile Gly Ile Asn Pro Ala Ser Gly Ser Ser Glu
    210                 215                 220

Glu Asp Tyr Glu Ala Arg Pro Leu Pro Pro Ala Asn Ser Asn Arg Leu
225                 230                 235                 240

Pro Pro Trp Met Ile Arg Ser Ala Asn Glu
                245                 250

<210> SEQ ID NO 40
<211> LENGTH: 252
<212> TYPE: PRT
<213> ORGANISM: Ananas comosus

<400> SEQUENCE: 40

Met Gly Arg Gly Pro Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Ala Leu Ile Val Phe
            35                  40                  45

Ser Thr Lys Gly Lys Leu Tyr Glu Tyr Ser Thr Asp Thr Ser Met Glu
50                  55                  60

Arg Ile Leu Asp Arg Tyr Glu Arg Tyr Ala Tyr Ala Glu Lys Ala Leu

```
                65                  70                  75                  80
Ser Glu Gly Tyr Pro Glu Ser Gln Gly Ser Trp Cys Glu Asp Tyr Gly
                    85                  90                  95

Lys Leu Lys Ser Lys Val Glu Ser Leu Gln Lys Lys Gln Arg Asn Leu
                100                 105                 110

Met Gly Glu Gln Leu Asp Ser Leu Thr Leu Lys Glu Leu Gln Gln Leu
            115                 120                 125

Glu Gln Gln Leu Asp Thr Ala Leu Arg His Ile Arg Ser Arg Lys Asn
        130                 135                 140

Gln Leu Leu Phe Asp Ser Ile Ser Glu Leu Gln Lys Lys Glu Lys Ser
145                 150                 155                 160

Leu Gln Glu Gln Asn Asn Ala Leu Glu Lys Leu Met Glu Lys Asp Ala
                165                 170                 175

Ala Asp Ala Asp Ala Asn Ala Leu Thr Gln His Leu Gln Trp Glu Gln
            180                 185                 190

Gln Asn Gln Pro Leu Thr Ser Pro Ser Pro Leu Pro Phe Val Phe Thr
        195                 200                 205

Asp Ala Leu Pro Asn Ser Asn Thr Gly Thr Tyr Gln Gln Ser Asp Thr
    210                 215                 220

Ser Cys Glu Pro Gly Ser Ala Glu Pro Leu Ile Asn Thr Asn Ser Lys
225                 230                 235                 240

Thr Leu Pro Pro Trp Met Leu Arg Leu Ala Asn Val
                245                 250

<210> SEQ ID NO 41
<211> LENGTH: 245
<212> TYPE: PRT
<213> ORGANISM: Dendrobium catenatum

<400> SEQUENCE: 41

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Ala Val Ile Val Phe
            35                  40                  45

Ser Asn Lys Gly Lys Leu Tyr Glu Phe Ser Thr Asp Ser Ser Met Glu
        50                  55                  60

Lys Ile Leu Glu Arg Tyr Glu Arg Tyr Ser Tyr Ala Glu Arg Ala Leu
65                  70                  75                  80

Phe Ser Asn Glu Ala Asn Pro Gln Ala Asp Trp His Leu Glu Tyr His
                85                  90                  95

Lys Leu Lys Ala Arg Val Glu Ser Leu Gln Lys Ser Gln Arg His Leu
                100                 105                 110

Met Gly Glu Gln Leu Asp Ser Leu Ser Ile Lys Glu Leu Gln His Leu
            115                 120                 125

Glu Gln Gln Leu Glu Ser Ser Met Lys His Ile Arg Ser Arg Lys Thr
        130                 135                 140

Gln Leu Ile Leu Asp Ser Ile Ser Glu Leu Gln Lys Lys Glu Lys Ile
145                 150                 155                 160

Leu Leu Glu Gln Asn Lys Thr Leu Glu Lys Glu Ile Ile Ala Lys Glu
                165                 170                 175

Lys Ala Lys Ala Leu Thr Gln Ile Ala Pro Trp Glu Lys Gln Asn Leu
            180                 185                 190
```

Ser Gln Tyr Ser Ser Ala Pro Leu His Val Ile Ser Asp Ser Val Pro
        195                 200                 205

Thr Pro Thr Arg Thr Phe Gln Ala Arg Ala Asn Glu Glu Ser Pro
        210                 215                 220

Gln Pro Gln Leu Arg Val Gly Asn Thr Leu Leu Pro Pro Trp Met Leu
225                 230                 235                 240

Ser His Ile Asn Gly
            245

<210> SEQ ID NO 42
<211> LENGTH: 245
<212> TYPE: PRT
<213> ORGANISM: Phalaenopsis equestris

<400> SEQUENCE: 42

Met Gly Arg Gly Arg Val Gln Leu Lys Arg Ile Glu Asn Lys Ile Asn
1               5                   10                  15

Gln Gln Val Thr Phe Ser Lys Arg Arg Ser Gly Leu Leu Lys Lys Ala
            20                  25                  30

His Glu Ile Ser Val Leu Cys Asp Ala Asp Val Ala Leu Ile Ile Phe
        35                  40                  45

Ser Asn Lys Gly Lys Leu Cys Glu Tyr Ser Thr Asp Ser Ser Met Glu
    50                  55                  60

Lys Ile Leu Glu Arg Tyr Glu His Tyr Ser Tyr Thr Glu Arg Ala Leu
65                  70                  75                  80

Tyr Ser Asn Glu Asp Asn Pro Gln Ala Asp Trp Arg Leu Glu Tyr Asn
                85                  90                  95

Lys Met Lys Ala Lys Val Glu Ser Leu Gln Lys Ser Gln Arg His Leu
            100                 105                 110

Met Gly Glu Gln Leu Asp Ser Leu Ser Ile Lys Glu Leu Gln His Leu
        115                 120                 125

Glu Gln Gln Leu Glu Ser Ser Leu Lys His Ile Arg Ser Arg Lys Thr
    130                 135                 140

Gln Leu Met Val Asp Ser Ile Ser Glu Leu Gln Lys Lys Glu Lys Leu
145                 150                 155                 160

Leu Leu Glu Gln Asn Lys Thr Leu Gln Asp Met Ala Lys Ala Lys Ala
                165                 170                 175

Lys Ala Leu Val Gln Asn Ala Ala Trp Glu Gln Gln Asn Lys Ser Gln
            180                 185                 190

Tyr Ser Ser Ala Pro Pro His Ala Val Ile Ser Asp Ser Val Pro Thr
        195                 200                 205

Pro Thr Ser Arg Thr Phe Arg Ala Arg Ala Asn Gly Glu Glu Ser Pro
    210                 215                 220

Gln Pro Gln Leu Arg Leu Gly Asn Thr Leu Leu Pro Pro Trp Met Leu
225                 230                 235                 240

Ser His Val Asn Gly
            245

<210> SEQ ID NO 43
<211> LENGTH: 250
<212> TYPE: PRT
<213> ORGANISM: Lilium formosanum x Lilium longiflorum

<400> SEQUENCE: 43

Met Gly Arg Gly Arg Val Gln Leu Lys Arg Ile Glu Asn Lys Ile Asn
1               5                   10                  15

```
Arg Gln Val Thr Phe Ser Lys Arg Ser Gly Leu Leu Lys Lys Ala
            20                  25                  30

His Glu Ile Ser Val Leu Cys Asp Ala Glu Val Ala Leu Val Phe
            35                  40                  45

Ser Ala Lys Gly Lys Leu Tyr Glu Tyr Ser Thr Asp Ala Ser Met Glu
50                      55                  60

Arg Ile Leu Glu Arg Tyr Glu Arg Tyr Ser Gln Ala Glu Arg Ala Val
65                  70                  75                  80

Lys Gln Gly Asp Thr Glu Ser Gln Gly Ser Trp Cys Leu Glu Tyr Ser
                85                  90                  95

Arg Leu Lys Ala Lys Ile Asp Val Leu Gln Lys Arg Gln Arg Gln Leu
            100                 105                 110

Met Gly Glu Gln Leu Asp Ser Cys Thr Leu Lys Glu Ile Gln Gln Leu
            115                 120                 125

Glu Gln Gln Leu Glu Thr Gly Leu Lys His Ile Arg Ser Arg Lys Asn
130                 135                 140

Gln Leu Leu Phe Asp Ser Leu Thr Glu Leu Gln Arg Lys Glu Arg Ser
145                 150                 155                 160

Leu Gln Glu Glu Asn Lys Ala Leu Glu Lys Val Leu Gln Glu His Lys
                165                 170                 175

Ala Lys Ala Leu Thr Gln Trp Glu Glu Gln Gln Gly Gln Pro His
            180                 185                 190

Thr Ser Thr Cys Leu Pro Ser Phe Leu Pro Val Glu His Leu Pro
            195                 200                 205

Thr Leu Asn Ile Gly Asn Tyr Gln Gly Arg Asp Asn Gly Pro Glu Asn
210                 215                 220

Glu Gly Ala Glu Ala Gln Pro Met Ala Gln Thr Asp Ser Asn Lys Leu
225                 230                 235                 240

Pro Pro Trp Met Leu Ser Arg Val Asn Gly
                245                 250

<210> SEQ ID NO 44
<211> LENGTH: 246
<212> TYPE: PRT
<213> ORGANISM: Dendrobium nobile

<400> SEQUENCE: 44

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Val Ile Val Phe
            35                  40                  45

Ser Asn Lys Gly Lys Leu Tyr Glu Phe Ser Thr Asp Ser Ser Met Glu
50                      55                  60

Lys Ile Leu Glu Arg Tyr Glu Arg Tyr Ser Tyr Ala Glu Arg Ala Leu
65                  70                  75                  80

Phe Ser Asn Glu Ala Asn Pro Gln Ala Asp Trp His Leu Glu Tyr His
                85                  90                  95

Lys Leu Lys Ala Arg Val Glu Ser Leu Gln Lys Ser Gln Arg His Leu
            100                 105                 110

Met Gly Glu Gln Leu Asp Ser Leu Ser Ile Lys Glu Leu Gln His Leu
            115                 120                 125

Glu Gln Gln Leu Glu Ser Ser Met Lys His Ile Arg Ser Arg Lys Thr
130                 135                 140
```

```
Gln Leu Ile Leu Asp Ser Ile Ser Glu Leu Gln Lys Lys Glu Lys Ile
145                 150                 155                 160

Leu Leu Glu Gln Asn Lys Thr Leu Glu Lys Glu Ile Ile Ala Lys Glu
                165                 170                 175

Lys Ala Lys Ala Leu Thr Gln Ile Ala Pro Trp Glu Lys Gln Asn Leu
            180                 185                 190

Ser Gln Tyr Ser Ser Ala Pro Leu His Val Ile Ser Asp Ser Val Pro
        195                 200                 205

Thr Pro Thr Ser Arg Thr Phe Gln Ala Ile Ala Asn Glu Glu Glu Ser
    210                 215                 220

Pro Gln Ala Gln Leu Arg Val Ser Asn Thr Leu Leu Pro Pro Trp Met
225                 230                 235                 240

Leu Gly His Met Asn Gly
                245
```

<210> SEQ ID NO 45
<211> LENGTH: 242
<212> TYPE: PRT
<213> ORGANISM: Musa acuminata subsp. malaccensis

<400> SEQUENCE: 45

```
Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

His Glu Ile Ser Val Leu Cys Asp Ala Glu Val Ala Leu Ile Ile Phe
            35                  40                  45

Ser Ala Lys Gly Lys Leu Tyr Glu Tyr Ser Thr Asp Ser Ser Met Glu
    50                  55                  60

Lys Ile Leu Gly Arg Tyr Glu Asn Tyr Trp Tyr Ala Glu Lys Ala Phe
65                  70                  75                  80

Ile Ser Ser Asp Leu Asp Ser Gln Gly Asn Trp Cys Gln Glu Tyr Arg
                85                  90                  95

Lys Leu Lys Ala Lys Leu Glu Ala Leu Ser Arg Ser Gln Arg His Leu
            100                 105                 110

Met Gly Glu Gln Leu Glu Ser Leu Asn Ile Arg Glu Leu Gln Gln Leu
        115                 120                 125

Glu His Gln Leu Glu Ile Ser Leu Lys His Val Arg Ser Arg Lys Asn
    130                 135                 140

Gln Val Met Phe Asp Ser Ile Ala Glu Leu Gln Ser Lys Glu Lys Ala
145                 150                 155                 160

Leu Gln Glu Gln Asn Met Asn Leu Glu Lys Gln Ile Val Glu Lys Gln
                165                 170                 175

Lys Ala Lys Val Val Asn Gln Gln Val His Trp Asp His Ala Gln Arg
            180                 185                 190

Ser Ser Ala Ser Pro Pro Ser Leu Met Ala Glu Ala Asp Pro Thr Phe
        195                 200                 205

Asn Ile Gly Pro Tyr Gln Gly Met Ala Ala Val Tyr Gly Gln His Gln
    210                 215                 220

Val Arg Thr Ser Asn Gly Leu Leu Pro Pro Trp Met Phe Arg Pro Leu
225                 230                 235                 240

Asn Gly
```

<210> SEQ ID NO 46

```
<211> LENGTH: 242
<212> TYPE: PRT
<213> ORGANISM: Ricinus communis

<400> SEQUENCE: 46
```

Met Gly Arg Gly Arg Val Gln Leu Lys Arg Ile Glu Asn Lys Ile Asn
1               5                   10                  15

Arg Gln Val Thr Phe Ser Lys Arg Ar

```
Lys Leu Lys Ala Lys Ile Glu Leu Leu Gln Arg Ser Gln Arg His Phe
                100                 105                 110

Leu Gly Glu Asp Leu Asp Ser Leu Ser Leu Lys Glu Leu Gln Asn Leu
            115                 120                 125

Glu Gln Gln Leu Asp Thr Ala Leu Lys His Ile Arg Ser Arg Lys Asn
        130                 135                 140

Gln Leu Met Tyr Glu Ser Ile Ser Glu Leu Gln Arg Lys Glu Lys Ala
145                 150                 155                 160

Met Gln Glu Gln Asn Asn Met Leu Ala Lys Glu Ile Lys Glu Lys Glu
                165                 170                 175

Lys Thr Val Ala Gln Gln Thr His Trp Glu Gln Gln Asn His Gly Leu
            180                 185                 190

Asn Thr Ser Ser Phe Leu Leu Pro Gln Gln Leu Pro Cys Leu Asn Met
        195                 200                 205

Gly Gly Thr Tyr Gln Gly Glu Ala His Gly Ala Arg Arg Asn Glu Leu
210                 215                 220

Asp Leu Thr Leu Glu Pro Ile Tyr Pro Ser His Leu Gly Cys Phe Thr
225                 230                 235                 240

Thr

<210> SEQ ID NO 48
<211> LENGTH: 258
<212> TYPE: PRT
<213> ORGANISM: Tulipa gesneriana

<400> SEQUENCE: 48

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Val Val Phe
        35                  40                  45

Ser Ala Lys Gly Lys Leu Tyr Glu Tyr Ser Thr Asp Ala Ser Met Asp
    50                  55                  60

Arg Ile Leu Glu Arg Tyr Glu Arg Tyr Ser Gln Ala Glu Arg Ala Val
65                  70                  75                  80

Thr Glu Ala Asp Pro Glu Ser Gln Ala Ser Trp Cys Leu Glu Tyr Gly
                85                  90                  95

Arg Leu Lys Ala Lys Ile Glu Val Leu Gln Lys Arg Gln Arg His Leu
            100                 105                 110

Met Gly Glu Gln Leu Glu Asn Cys Thr Leu Lys Glu Ile Gln Gln Leu
        115                 120                 125

Glu Gln Gln Leu Glu Thr Ala Leu Lys His Ile Arg Thr Arg Lys Asn
    130                 135                 140

Gln Leu Leu Tyr Asp Ser Ile Thr Glu Leu Gln Gln Lys Glu Arg Thr
145                 150                 155                 160

Leu Gln Glu Gln Asn Lys Thr Leu Glu Lys Leu Leu Glu Glu Gln Lys
                165                 170                 175

Ser Lys Ala Ser Ala Gln Trp Glu Gln Gln Pro Gln Gln Gln Gln Gln
            180                 185                 190

Gln Gln Gly Gln Pro His Ala Asn Asn Cys Ser Pro Ser Phe Leu Leu
        195                 200                 205

Ser Ala Asp Pro Phe Pro Thr Leu Asn Met Gly Thr Tyr Gln Ala Arg
    210                 215                 220
```

Gly Ser Ser Asn Glu Glu Asp Gly Ala Thr Ala Gln Ala Gln Pro Leu
225                 230                 235                 240

Ala Arg Pro Gly Ser Asn Lys Leu Pro Pro Trp Met Leu Ser His Val
            245                 250                 255

Asn Gly

<210> SEQ ID NO 49
<211> LENGTH: 242
<212> TYPE: PRT
<213> ORGANISM: Daucus carota subsp. sativus

<400> SEQUENCE: 49

Met Gly Arg Gly Lys Val Gln Leu Lys Arg Ile Glu Asn Lys Ile Asn
1               5                   10                  15

Arg Gln Val Thr Phe Ser Lys Arg Arg Gly Gly Leu Leu Lys Lys Ala
            20                  25                  30

His Glu Ile Ser Val Leu Cys Asp Ala Glu Val Ala Leu Ile Val Phe
        35                  40                  45

Ser Asn Lys Gly Lys Leu Phe Glu Tyr Ser Thr Asp Ser Ser Met Glu
    50                  55                  60

Glu Ile Leu Glu Arg Tyr Glu Arg Tyr Ser Tyr Ala Glu Arg Gln Val
65                  70                  75                  80

Ile Ala Asn Asp Pro Glu Ser Thr Gly Asn Trp Thr Leu Glu Tyr Thr
                85                  90                  95

Lys Leu Lys Ala Arg Ile Asp Leu Leu Gln Arg Asp His Arg His Tyr
            100                 105                 110

Met Gly Glu Asp Leu Asp Ser Leu Thr Leu Lys Glu Ile Gln Asn Leu
        115                 120                 125

Glu Gln Gln Leu Asp Thr Ala Leu Lys His Ile Arg Ser Arg Lys Asn
130                 135                 140

Gln Leu Ile Phe Glu Ser Ile Ser Asp Leu Gln Lys Lys Glu Lys Ala
145                 150                 155                 160

Ile Gln Glu Glu Asn Gly Lys Leu Thr Lys Lys Ile Lys Glu Arg Glu
                165                 170                 175

Lys Thr Met Val Gln Gln Ala Gln Trp Glu Lys Gln Asn Pro Ser Pro
            180                 185                 190

Asn Leu Ser Thr Phe Leu Met Pro Gln Glu Asn Pro Phe Leu Asn Ile
        195                 200                 205

Gly Gly Thr Phe Gln Gly Glu Ser Ser Gln Gly Met Thr Arg Asn Asp
210                 215                 220

Leu Asp Leu Thr Leu Glu Pro Asn His Tyr Pro Cys Asn Leu Arg Cys
225                 230                 235                 240

Phe Ala

<210> SEQ ID NO 50
<211> LENGTH: 244
<212> TYPE: PRT
<213> ORGANISM: Papaver atlanticum

<400> SEQUENCE: 50

Met Gly Arg Gly Arg Val Gln Leu Lys Arg Ile Glu Asn Lys Ile Asn
1               5                   10                  15

Arg Gln Val Thr Phe Ser Lys Arg Arg Ser Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Phe Glu Tyr Ser Thr Asp Ser Gly Met Asp
 50                  55                  60

Arg Ile Leu Glu Arg Tyr Glu Arg Tyr Ser Tyr Ala Glu Arg Glu Leu
 65                  70                  75                  80

Val Thr Thr Glu Ile Asp Gln Gly Asn Trp Ser Leu Gly Tyr Ser Lys
                 85                  90                  95

Leu Lys Ser Lys Ile Glu Ile Leu Gln Lys Asn Gln Arg His Phe Met
                100                 105                 110

Gly Glu Asp Leu Arg Ser Met Ser Leu Lys Glu Leu Gln Asn Leu Glu
                115                 120                 125

Gln Gln Leu Asp Val Ala Leu Lys Gln Ile Arg Ser Arg Lys Asn Gln
130                 135                 140

Leu Met Tyr Glu Ser Ile Ser Glu Leu Gln Lys Lys Glu Lys Ala Leu
145                 150                 155                 160

Gln Glu Gln Asn Asn Lys Leu Gly Lys Gln Leu Lys Glu Lys Glu Lys
                165                 170                 175

Glu Val Ala Ala Lys Gln Gln Gln Ala Ser Gln Phe Ser Gln Gly Gln
                180                 185                 190

Ser Ser Pro Ser Phe Leu Leu Ser Gln Ser Leu Pro Ser Leu Asn Ile
                195                 200                 205

Gly Ser Gly Ser Tyr Gln Ala Arg Gly Gly Asp Asn Gly Asn Glu Glu
                210                 215                 220

Gly Asn Arg Thr Gln Thr Thr Arg Thr Asn Thr Ala Thr Leu Met Pro
225                 230                 235                 240

Gln Trp Met Leu

<210> SEQ ID NO 51
<211> LENGTH: 239
<212> TYPE: PRT
<213> ORGANISM: Theobroma cacao

<400> SEQUENCE: 51

Met Gly Arg Gly Arg Val Gln Leu Lys Arg Ile Glu Asn Lys Ile Asn
 1                  5                  10                  15

Arg Gln Val Thr Phe Ser Lys Arg Arg Ser Gly Leu Leu Lys Lys Ala
                 20                  25                  30

His Glu Ile Ser Val Leu Cys Asp Ala Glu Val Ala Leu Ile Val Phe
                 35                  40                  45

Ser Thr Lys Gly Lys Leu Phe Glu Tyr Ser Thr Asp Ser Cys Met Glu
 50                  55                  60

Arg Ile Leu Glu Arg Tyr Glu Arg Tyr Ser Tyr Ala Glu Arg Gln Leu
 65                  70                  75                  80

Ala Gly Asn Glu Val Asp Gln Asn Gly Ser Trp Thr Leu Glu His Ala
                 85                  90                  95

Lys Leu Lys Ala Arg Met Glu Val Leu Gln Arg Asn Gln Arg His Phe
                100                 105                 110

Met Gly Glu Asp Leu Asp Asn Leu Ser Leu Arg Glu Leu Gln Asn Leu
                115                 120                 125

Glu Gln Gln Leu Asp Ser Ala Leu Lys His Val Arg Ser Arg Lys Asn
130                 135                 140

Gln Leu Met Phe Glu Ser Ile Ser Glu Leu Gln Lys Lys Asp Lys Ala
145                 150                 155                 160

Leu Gln Glu Gln Asn Asn Met Leu Ala Lys Lys Val Lys Glu Lys Glu
                165                 170                 175

```
Gln Ala Val Ala Gln Gln Ala Gln Trp Glu Gln Gln Asn Asn Cys Gln
            180                 185                 190

Asp Thr Ser Ala Ile Leu Leu Pro Gln Pro Met Ser Gly Thr Tyr Glu
        195                 200                 205

Ala Arg Ser Ser Gly Arg Glu Glu Gly Asn Pro Ala Gln His Arg
    210                 215                 220

Gly Ala Asn Ala Leu Leu Pro Pro Trp Met Ile Arg His Leu Glu
225                 230                 235

<210> SEQ ID NO 52
<211> LENGTH: 5102
<212> TYPE: DNA
<213> ORGANISM: Oryza sativa

<400> SEQUENCE: 52
```

| | | | | | |
|---|---|---|---|---|---|
| ccaatcggaa | atcgacaacg | aggcactcga | aaccgccctg | gtatggccac | accgcattcc | 60 |
| accccatct | aaaaccgcct | tccctccccc | tccctctctc | ttcctccccc | catttccatc | 120 |
| ttccccgagc | tctccaccct | ccacccgcca | ccgccaccgc | cgccttcgcc | gccgccgccg | 180 |
| ccgccgacga | cgatggggag | agggccggtg | cagctgcggc | ggatcgagaa | caagataaac | 240 |
| aggcaggtga | ccttctccaa | gcggaggaac | gggctgctga | agaaggcgca | cgagatctcc | 300 |
| gtgctctgtg | acgccgacgt | cgcgctcatc | gtcttctcca | ccaagggcaa | gctctacgag | 360 |
| ttctccagcc | actccaggta | cgcacgcgct | tagctcctcc | tcctcctcct | cctcctctcc | 420 |
| gcgacctccc | gcctacctac | gtagtacggc | ccatgcccgt | cgcctttcct | cgccgcgcgc | 480 |
| gcgccatggg | cgagctcgcg | gagctccccg | ttcctgggcg | gcttgttgat | gcgttcgatt | 540 |
| tcgtttcgta | cgggttcctg | ccttgtgttc | gatcgtttcc | gctgcggaat | gcgaggggc | 600 |
| tggtggtgtt | ggtgcgtgta | cgattgctat | tatttcgtgc | tgattgattt | ctctcatgtg | 660 |
| ctctctgatt | gcacatacgg | ttcatggctt | tgtacgtgtt | cgttcgtgcg | attgctgctt | 720 |
| agctcgggat | ggagttgctc | gcgaagtcta | gctagttgta | ggttgcttgt | gtcccctgga | 780 |
| ttacagctct | ctatgtgatg | ctggcatgct | gctgctgctg | ctgccatgca | tatcagaagc | 840 |
| tagtaatata | cagtggtggt | acatgcactg | ttgctgattt | agctttatat | gctgctcagt | 900 |
| tttgttcttg | gggactcatc | aatcatcgta | gcattggtga | acacgttcac | ttccattttt | 960 |
| ttttgtataa | aaaggaatgg | aataataggt | gaaaaaaat | tcatgtgctt | catcagtacg | 1020 |
| ggcggaaaga | aagatatgtt | taaatttta | ttagtgtgct | tatctaggtt | tatcatatgc | 1080 |
| ttatactctt | gtgtactgta | gcatatacaa | gtgatgctta | ttaccaaagc | ctagctaggc | 1140 |
| cggtaaactt | gtattatttg | tctcgttatt | tctggaaatc | attagagcag | cacttcagtt | 1200 |
| gaaatatgca | cggacgcctt | gctaattaag | cggctcctct | aaccaggcca | gtaaggtctt | 1260 |
| aagttactga | caactcctgg | actggtataa | atggcgcggc | cagctttaca | tgacatatgg | 1320 |
| tttgatactt | ttgtttagtt | aatttcgagg | tggaatataa | ggtgaccagc | ttacttaact | 1380 |
| tgttcatttg | atgcattcgg | tttcatttcc | cttttttttt | ttaagataat | gggaagtaaa | 1440 |
| ttaatacccg | gccttgcttt | aactgaaact | acaactttct | tttgtcccctt | tagtgtgtac | 1500 |
| tgtcaccaag | ttagctatac | atggtgcaag | ttgccattgc | ccattgctat | taacttgctc | 1560 |
| tcacaaattg | gggtgtttat | ttcttgaaat | ggattttta | ggacaacaat | aaactgattg | 1620 |
| acatagctat | actgttcaag | tataaccatg | tttatggttt | tcaattaagc | aaactgctta | 1680 |
| tgtttatgct | aatatctttt | gtttaatggg | aggaatttaa | atatttcatt | attggtattc | 1740 |

-continued

```
ctatactcta ttatttcata atatttggca attttgaccg gtgattgctt cagtttaacc    1800
attaatatct tttaaaattt atgattatga tggatgggat ttatatctct atatttacca    1860
ttaccatgta acatacttta ataatatgtt acataatcta atactaaaag tttatttata    1920
aaattggaat ggccaaacta aaacaatgcg aacttaaaat caccaagtat tatgaaatgg    1980
agggagcata atatcagtag ctcgtaaggg aaaaaaggga cctaaatgat gccttttgtg    2040
ataaatataa tttcaaattt gcaaaatttt tggataggca acaatactct ctcattattg    2100
tgttagtatt aaggtcaagc tacttctatg ctaccaaata ctccttctgt tcctttttt    2160 atttcttgtc taggatattg acattatccc taacacacat ctttctttgt atgatcatct    2220
actcataaaa tagttaaaat ataactacat tattcaatta tgaatctatg aatgttattt    2280
ttatacaccg agttgggaac tattctaaac tctcgagggg acatcccctc attatctgca    2340
tgttatccaa acggttgtga aaaaaattga aaaaaaataa acaagataga ttaatatgtg    2400
ataaatcact ccacaaacat gcaaggacaa attcaaattc tacaagttgc aatgaaaaaa    2460
ttaaatttga ccgtgaatat acattaacta gccatagttt aattttttt tgttgtaact    2520 tgtagaagtt gaatttgaac ttgcatgttt gtgaagtaat ctatcacata ttaatctatc    2580
ttgtcgattt ttttttaaaa aaatcataac catttagatg acatgcaaaa aacgagggga    2640
tgttcccttg agagtttaga atccattctc cagtgagttg atgttgagat ttgattacac    2700
atttcaaaac gacttttatt tgttaacgaa gggagtaatg tggattcacc atatgtacta    2760
atgttattaa ggccagataa tccttttttt aatcattcta attagatata aacttacgac    2820
gaagaacatg aatggataaa gtttcagcca acaaatacaa atgttttca aagtgctatt    2880 tctgatgcat aattttgta gcagttatga tttaaattta tacatggata atttgaataa    2940
tggatcctac ttttgtagtt gtcacctgac aagccttaag aattattgag ggtacaaaaa    3000
ttataactgt gcatttgttt gatattgctc taagactatg cttggcatca tcttttgatg    3060
cattggtcaa accaaagcat aatcatgtga tacttcttct gtagtatgga agggatcctt    3120
gaacgctacc agcgttactc gtttgatgaa agagccgtac tggagccaaa tactgaggac    3180
caggtaaaaa aacatccctg actgttggag aactatctcc ggctgtttat ttaactagct    3240
ggttagttat ctgatcttga tattcatttt ctcctaggaa aactggggtg atgaatatgg    3300
aattttgaag tccaaactgg atgcacttca gaagagccaa aggtactgca aacttcttta    3360
agaaattttc actttggtaa caagattatg ctaacttgag ttggtctatc tactgctcaa    3420
ggcaactctt aggtgaacaa ttggacacac taacaataaa agaactccag caattggaac    3480
atcaactgga atattctctg aagcatataa gatcaaaaaa ggtgaaattt gtgtccatta    3540
tgcactgttg actgagggat caaatttgct tgatttaatt atttccaact aatctttgaa    3600
aacatcatta ctttccttt tgttttctt ttgcagaatc agcttctgtt tgaatcaatt    3660
tctgagcttc agaagaaggt aggttaccct caatgtggct ccttaaatag caatgtagca    3720
gtctgtttat accatattgt tttggagtat taaagttgca ttcaaacaat tttcagacaa    3780
ctaactcttc ttgccttcta ccagaatata ttcatgtaaa acatgtcttt tggcaattct    3840
agaaattcca ttataagaag aaatcattag tcaatttgaa tcacctaagg aactaacgag    3900
aagccacttg tcttggtcat attgtgggaa atgcacaatg ttgtcaaatg ggtataacag    3960
gaaagtcgcc atcaatgtat atattctagg ggagagagaa cagactaagt cagactacgt    4020
tgtaaaattg aacattctac gggaaaataa atcttcgatg catatggcaa ggacttgacc    4080
gttagccttt tacgcaataa tgtatgcata aacataggga aaaaaagga cctgcactac    4140
```

```
tgattgttac tgtatctgat ctggcaagtg gcaacagagc catgttaata ttgtgctgag    4200
aaatggacga agttgatata ggttcgtgct gatgaatatt cttacaatct gctatcttcc    4260
tgtctgcagg aaaagtcact taaaaaccag aataatgttc tgcaaaaggt aaatttcatt    4320
cttgtttaca acaatgtttt atatcagatc actacaaaag ctgtattgga ggtcaaaccc    4380
ttttgtctac attcttcgga gcagctcatg gagacagaaa aggagaaaaa caatgctata    4440
ataaacacta accgggagga gcaaaatgga gcaacaccaa gcacatcatc accaacacca    4500
gtgacggctc cagatcccat cccgacaaca aataacaggt accgctttta cttccatata    4560
ttttgcccct gcactcacca taaataaaac aaaactctgt tttgttcttc agcaaatttt    4620
tattctatat tttttctttt atcagacttc cattatctat cacagttcag tagtttttga    4680
tggtctatgc ctaggaaact taatccggtg aaatttgttc aatcaaatgc tgccggtcta    4740
tttcatatgg ctattggaag tttggaacaa ataagcccag gcctgaaagc gcctgaacca    4800
aacagtgaaa aagcctccaa atggtttggt ctcagcttga tatatcatgt ctgaacaata    4860
acttgacgtt aggaatgatc tagcatgtta ctactatttc atcaactcca ttgtctgttt    4920
tagttatgct gtttttcctc atcttaattc agtcaaagcc aaccaagagg atcaggggag    4980
tcagaagctc aaccgtctcc ggcacaagca ggcaacagca agcttccgcc atggatgctc    5040
cggacaagtc acacatgaag gcatctgttg atctcaaacg tcactccact caatggccaa    5100
ca                                                                  5102
```